(12) United States Patent
Sepe et al.

(10) Patent No.: US 11,361,394 B1
(45) Date of Patent: **\*Jun. 14, 2022**

(54) PRESCRIPTION STOCK MANAGEMENT SYSTEM

(71) Applicant: WALGREEN CO., Deerfield, IL (US)

(72) Inventors: Paolo Sepe, Naples (IT); Richard Ian Naylor, Derbyshire (GB); Sarah Helen Scriver, Nottingham (GB); Giovanni Passarella, Naples (IT); Farid Poonja, Epsom (GB); Neil Younger, Lincoln (GB)

(73) Assignee: WALGREEN CO., Deerfield, IL (US)

( * ) Notice: Subject to any disclaimer, the term of this patent is extended or adjusted under 35 U.S.C. 154(b) by 105 days.

This patent is subject to a terminal disclaimer.

(21) Appl. No.: 16/825,197

(22) Filed: Mar. 20, 2020

Related U.S. Application Data

(63) Continuation of application No. 15/042,836, filed on Feb. 12, 2016, now Pat. No. 10,621,687.

(51) Int. Cl.
| | |
|---|---|
| *G06Q 10/06* | (2012.01) |
| *G06Q 10/08* | (2012.01) |
| *G06Q 20/20* | (2012.01) |
| *G06Q 50/22* | (2018.01) |

(52) U.S. Cl.
CPC ....... *G06Q 50/22* (2013.01); *G06Q 10/06315* (2013.01); *G06Q 10/087* (2013.01); *G06Q 20/203* (2013.01)

(58) Field of Classification Search
CPC .................. G06Q 50/22; G06Q 10/06315
See application file for complete search history.

(56) References Cited

U.S. PATENT DOCUMENTS

| | | | |
|---|---|---|---|
| 6,249,774 B1 * | 6/2001 | Roden .................. | G06Q 10/087 705/28 |
| 2007/0043469 A1 * | 2/2007 | Draper ...................... | G07F 9/02 700/231 |

FOREIGN PATENT DOCUMENTS

| | | | | |
|---|---|---|---|---|
| CA | 2834539 A1 * | 5/2014 | ............. | G07F 11/44 |

\* cited by examiner

*Primary Examiner* — Eliza A Lam
(74) *Attorney, Agent, or Firm* — Marshall, Gerstein & Borun LLP; Randall G. Rueth

(57) ABSTRACT

Techniques for automatically tracking, ordering, and replenishing prescription item stock are provided. Based upon a statistical analysis of prescription order transactions, rules may be established to selectively identify which prescription stocked items qualify for automatic stock tracking, ordering, and replenishment. The rules may be based upon metrics such as a daily rate at which each prescription item is dispensed over a specified sampling period as well as the cost of each prescription item. Once qualified, automatic replenishment may be facilitated by calculating stock number minimums and maximums using a statistical analysis of the prescription transaction history for qualifying prescription items. The minimum and maximum stock number values may be used to trigger the generation of purchase orders and to specify how much stock needs to be ordered for each qualifying prescription item as it is replenished.

20 Claims, 9 Drawing Sheets

Grid Maintenance

| RANGING | MIN | MAX | TAF |
|---|---|---|---|

| 9999 | Yes | Yes | Yes | Yes | Yes | Yes | No |
|---|---|---|---|---|---|---|---|
| 72 | Yes | Yes | Yes | Yes | Yes | Yes | No |
| 28 | Yes | Yes | Yes | Yes | Yes | Yes | No |
| 2 | No | No | No | No | No | No | No |
| DAILY FREQUENCY SCRIPTS / RANGING COST | 0 | 0.5 | 2.5 | 20 | 50 | 100 | 200 | 9999 |

Grid Code: 00141

**Grid Name*:** Cripps Store Only

**Grid Description*:** Grid for Cripps following feedback 22/12/14 and then update Jan 19th

Comments of previous updates: Updated by RN

Grid Structure | Grid Association

Nr. Stores Associated: 1

Comment: [ ]

Cell Options
○ Yes
○ No
○ Exclude

[Apply]

Grid Maintenance — 406

RANGING [MIN|MAX] TAF — 402, 404, 408

| DAILY FREQUENCY SCRIPTS | | | | | | | |
|---|---|---|---|---|---|---|---|
| 9999 | TAF uplift for a defined period | No TAF uplift | No TAF uplift | No TAF uplift | No TAF uplift | No TAF uplift | No TAF uplift |
| 72 | | | | | | | |
| | No TAF uplift | No TAF uplift | No TAF uplift | No TAF uplift | No TAF uplift | No TAF uplift | No TAF uplift |
| 28 | | | | | | | |
| | No TAF uplift | No TAF uplift | No TAF uplift | No TAF uplift | No TAF uplift | No TAF uplift | No TAF uplift |
| 2 | | | | | | | |
| | No TAF uplift | No TAF uplift | No TAF uplift | No TAF uplift | No TAF uplift | No TAF uplift | No TAF uplift |
| 0 | 0.5 | 2.5 | 20 | 50 | 100 | 200 | 9999 |

RANGING COST

Grid Code: 00141 — 410
Grid Name*: Cripps Store Only — 412
Grid Description*: Grid for Cripps following feedback 22/12/14 and then update Jan 19th — 418
Nr. Stores Associated: 1 — 414
[Grid Structure] [Grid Association] — 411, 409
Comment: — 416
Comments of previous updates: Updated by RN — 419

Cell Options — 462
○ TAF uplift for a defined period
○ No TAF uplift
[Apply]

FIG. 4D

PRESCRIPTION STOCK MANAGEMENT SYSTEM

CROSS REFERENCE TO RELATED APPLICATION

This application is a continuation of U.S. patent application Ser. No. 15/042,836, filed Feb. 12, 2016, the disclosure of which is incorporated herein by reference in its entirety.

TECHNICAL FIELD

The present disclosure generally relates to techniques for automatically tracking, ordering, and replenishing prescription item stock and, more particularly, to techniques utilizing a statistical analysis of prescription order transactions to identify prescription items that qualify for stock tracking, when to order additional stock, and how much stock to order.

BACKGROUND

Stock tracking and ordering for prescription drugs differs from traditional stock inventory tracking associated with retailers. Some of these differences may be attributed to retailer stock being promotionally driven and, as a result, somewhat predictable. Furthermore, prescription drugs, if ordered too soon or in too great amount, risk expiration prior to sale, thereby increasing the cost borne by the pharmacy.

Optimally, prescription stock should be sold prior to expiring but with enough cover on hand in the event that demand outpaces the rate at which new stock may be ordered and replenished. However, attempts to do so have conventionally required a great deal of observation, inventory, and manual ordering of new prescription drugs on a per-store level. And based upon the somewhat unpredictable nature of prescription drug sales, manual ordering may result in an inventory overstock or shortage. To further complicate matters, the rate at which some prescription items are dispensed and their cost may greatly differ among stocked prescription items at a single pharmacy. Because it is undesirable to risk overstocking more expensive prescription items, traditional stock ordering processes force pharmacies to order new stock more frequently for prescription items for that are more often dispensed and/or have a lower cost, which complicates the ordering process.

As a result, automatic stock tracking and ordering is useful but presents several challenges.

SUMMARY

In an embodiment, a centralized computing device is provided that functions to bridge several networks and/or pharmacy locations together. The centralized computing device may function to aggregate and store prescription item transactions from several pharmacy locations and make this data accessible to pharmacy computers at each pharmacy location, other third parties, and/or other computing devices. The one or more computing devices may run one or more applications and/or user interfaces that facilitate the selection of various rule parameters, which may be applied to each prescription item to identify whether a prescription item qualifies for automatic stock tracking, ordering, and replenishment.

The rule parameters may leverage specific metrics calculated from a statistical analysis of the prescription item transactions for a specified sampling period, for each prescription item, to determine which prescription items qualify for automatic stock tracking, ordering, and replenishment. In an embodiment, the rule parameters may specify various ranges of average daily dispensing frequency values of a prescription item over the sampling period and a range of costs of the prescription, which need to be met for a prescription item to qualify for automatic stock tracking, ordering, and replenishment.

Furthermore, once a prescription item qualifies for automatic stock tracking, ordering, and replenishment, embodiments include using additional metrics calculated from the prescription item transactions to set a minimum stocked number. The minimum stocked number may act as a threshold that triggers a purchase order being generated once the prescription item stock inventory falls below this number. In addition, the metrics may be used to calculate a maximum stocked number of prescription items to keep on hand in the pharmacy. Rule parameters may also provide for exceptions that may apply to specific pharmacy locations, regions, countries, specific dates, etc., to provide additional flexibility and to ensure that the appropriate amount of prescription items are ordered at the right time and in the right amounts.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, whenever possible, the following description refers to the reference numerals included in the following figures, in which features depicted in multiple figures are designated with consistent reference numerals.

FIG. 4A illustrates an exemplary user interface screen 400 to facilitate the determination of whether a prescription item qualifies for automatic stock tracking in accordance with an exemplary embodiment of the present disclosure;

FIG. 4B illustrates an exemplary user interface screen 420 to facilitate the calculation of a minimum stocked number for a qualifying prescription item in accordance with an exemplary embodiment of the present disclosure;

FIG. 4C illustrates an exemplary user interface screen 440 to facilitate the calculation of a maximum stocked number for a qualifying prescription item in accordance with an exemplary embodiment of the present disclosure;

FIG. 4D illustrates an exemplary user interface screen 460 to facilitate the calculation of one or more rule exceptions to apply to one or more qualifying prescription items in accordance with an exemplary embodiment of the present disclosure;

DETAILED DESCRIPTION

The following text sets forth a detailed description of numerous different embodiments. However, it should be understood that the detailed description is to be construed as exemplary only and does not describe every possible embodiment since describing every possible embodiment would be impractical. One of ordinary skill in the art will recognize, in light of the teaching and disclosure therein, that numerous alternative embodiments could be implemented.

Although the embodiments described throughout the disclosure are explained in the context of a retail store, other embodiments of the present disclosure include non-retail contexts as well. For example, in some embodiments, the actions executed upon identification of one or more trigger conditions may be related to evaluations or surveys in a non-retail context.

It should be understood that, unless a term is expressly defined in this patent application using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent application.

Furthermore, the embodiments described herein provide several advantages of a technical nature in addition to traditional techniques for tracking and ordering prescription item stock. For example, by providing a system whereby a statistical analysis of prescription item transactions are used as the basis of when to order additional stock, the efficiency of this process is improved over manual methods that do not use this data. This improved efficiency not only results in less labor, but also results in less unnecessary purchase orders being generated. Therefore, the embodiments described herein improve the technical aspects of existing technology by reducing bandwidth required to submit additional purchase orders and also reduce the overall power consumption of traditional systems.

In addition, by integrating and aggregating prescription item stock transactions from a pool of pharmacies, rules may be applied to a greater umbrella of pharmacy locations that would otherwise be possible. As a result of this breadth of rule applications, several stores may potentially gain the advantages described herein from a single set of rules. This represents an improvement in data processing and data organization from existing technologies that yields a real and tangible improvement from the systems in use today that do not provide pharmacy data aggregation and integration.

Figure 1:
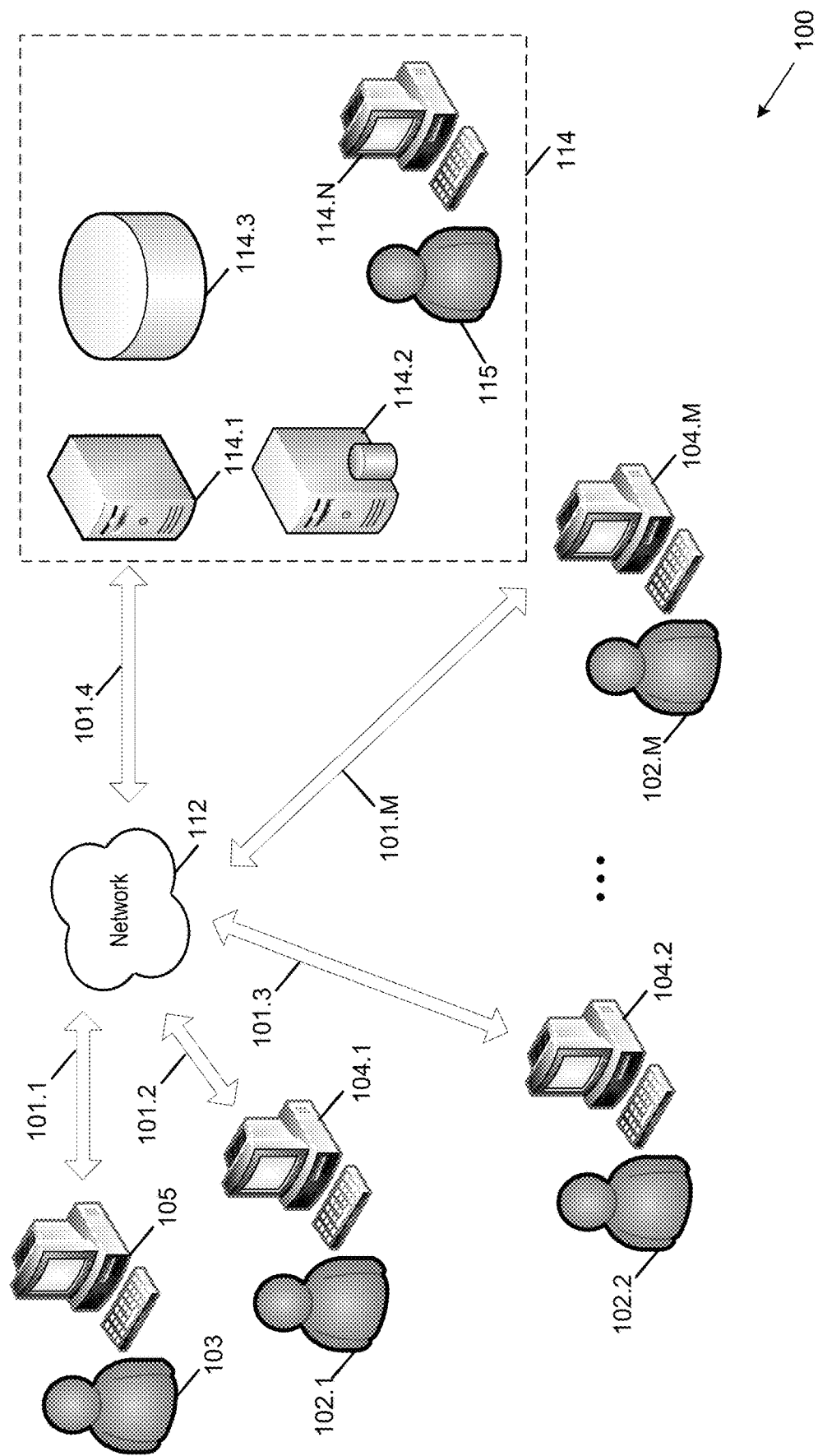
FIG. 1 illustrates a block diagram of an exemplary prescription item stock management system 100 in accordance with an exemplary embodiment of the present disclosure.

FIG. 1 illustrates a block diagram of an exemplary prescription item stock management system 100 in accordance with an exemplary embodiment of the present disclosure. Exemplary prescription item stock management system 100 includes any suitable number 'M' of computing devices 104.1-104.M, which may be associated with or operated by users 102.1-102.M (e.g., a pharmacist and/or a pharmacy technician), one or more computing devices 105, which may be associated with or operated by user 103 (e.g., a third party user, warehouse personnel, wholesale store personnel, etc.), a communication network 112, and a central hosting service 114, which may include any suitable number 'N' of external computing devices 114.1-114.N.

Generally, exemplary prescription item stock management system 100 may facilitate users 102.1-102.M accessing prescription item information for the various patients that have been prescribed prescription items (e.g., prescription drugs), entering in the details of when a prescription item has been dispensed, and ordering stock to replenish dispensed prescription items.

Furthermore, exemplary prescription item stock management system 100 may facilitate user 103 accessing central hosting service 114 and/or otherwise viewing order information that is stored on one or more of external computing devices 114.1-114.N. As will be further discussed below, this order information may include, for example, information related to pending orders about to be placed with the third party associated with user 103 and computing device 105, prescription stock files transmitted from one or more computing devices 104.1-104.M to central hosting service 114, details regarding purchase orders manually transmitted or otherwise sent to central hosting service 114 via one or more computing devices 104.1-104.M, etc.

Therefore, computing devices 104.1-104.M and 105 may be implemented as any suitable number and/or type of computing devices configured to provide a user interface to facilitate user interaction and to communicate with central hosting service 114. In an embodiment, each of computing devices 104.1-104.M and 105 may be located in a separate physical store or location. For example, each of computing devices 104.1-104.M may be located or otherwise associated with a separate pharmacy location, while computing device 105 may be located at or otherwise associated with a third party prescription item ordering service, warehouse, wholesaler, delivery service, etc. In an embodiment, computing devices 104.1-104.M may form a network of pharmacy computers, which may belong to the same pharmacy region (e.g., pharmacy locations within a city or within a particular portion of a city), pharmacy locations within a group of regions, pharmacy locations within the same country, pharmacy locations within a group of countries or separate countries, etc.

In various embodiments, computing devices 104.1-104.M and/or computing device 105 may be implemented as computer terminals, laptop computers, desktop computers, tablet computers, computer terminals, etc., which may be configured to allow a respective user (e.g., users 102.1-102.M and/or user 103) to query and/or update customer information, order information, and/or prescription information stored in central hosting service 114 (i.e., in one or more external computing devices 114.1-114.N). Additionally or alternatively, one or more users 102.1-102.M may use a respective computing device 104.1-104.M to enable store-to-store prescription filling. In an embodiment, one or more computing devices 104.1-104.M and/or 105 may provide respective one or more users 102.1-102.M and/or 103 with secure access to one or more external computing devices 114.1-114.N. For example, computing device 104.1 may facilitate secure sign on and/or authentication procedures to allow user 102.1 to access one or more external computing devices 114.1-114.N via communication network 112.

Computing devices 104.1-104.M and/or computing device 105 may be configured to communicate with central hosting service 114 via communication network 112 using any suitable number and/or type of communications protocols in conjunction with any suitable number and/or type of wired and/or wireless links. For example, one or more computing devices 104.1-104.M and/or computing device 105 may be coupled to communication network 112 via one or more landline, Internet Service Provider (ISP) backbone connections, satellite links, public switched telephone networks (PSTNs), etc., which may be represented as links 101.1-101.M, for example, as shown in FIG. 1.

Communication network 112 may be configured as any suitable network configured to facilitate communications between one or more computing devices 102.1-102.M, computing device 105, and central hosting service 114. For example, communication network 112 may be coupled to one or more external computing devices 114.1-114.N via one or more landline, Internet Service Provider (ISP) backbone connections, satellite links, public switched telephone networks (PSTNs), etc., which may be represented as link 101.4, for example, as shown in FIG. 1.

To provide additional examples, communication network 112 may include a proprietary network, a secure public internet, a mobile-based network, a virtual private network, etc. Communication network 112 may include any suitable number of interconnected network components that form an aggregate network system, such as dedicated access lines, plain ordinary telephone lines, satellite links, cellular base stations, a public switched telephone network (PSTN), etc., or any suitable combination thereof.

In some embodiments, communication network 112 may facilitate one or more computing devices 102.1-102.M and/or computing device 105 connecting to the Internet. In embodiments in which communication network 112 facilitates a connection to the Internet, data communications may take place over communication network 112 via one or more suitable Internet communication protocols. In various embodiments, communication network 112 may be implemented, for example, as a wireless telephony network (e.g., GSM, CDMA, LTE, etc.), a Wi-Fi network (e.g., via one or more IEEE 802.11 Standards), a WiMAX network, etc.

Again, central hosting service 114 may include one or more external computing devices 114.1-114.N, which may be implemented as any suitable number of components configured to store data, receive data from one or more computing devices 102.1-102.M and/or computing device 105 (or one another), and/or send data to one or more computing devices 102.1-102.M and/or computing device 105 (or one another) via communication network 112 or any other suitable combination of wired and/or wireless links. In various embodiments, one or more external computing devices 114.1-114.N may be configured to execute one or more applications to facilitate one or more aspects of the functionality used in accordance with one or more embodiments as discussed herein.

For example, one or more external computing devices 114.1-114.N may be implemented as one or more back-end components, which may include computing and/or storage devices such as one or more back end servers 114.1, one or more database servers 114.2, one or more databases 114.3, and/or one or more external computing devices 114.N. Although FIG. 1 illustrates central hosting service 114 as including only four different types of back-end components, it will be appreciated that central hosting service 114 may include any suitable number and/or type of back-end components to facilitate the appropriate functions of the embodiments as described herein.

For example, back-end server 114.1 may be implemented as any suitable number of web servers configured to provide Internet communications to one or more computing devices 104.1-104.M and/or computing device 105 and/or to support one or more applications installed on one or more computing devices 104.1-104.M and/or computing device 105.

To provide another example, database server 114.2 may be implemented as any suitable number and/or type of servers that are configured to access data from database 114.3, which may store data such as a history of placed orders (e.g., via computing device 105), current orders, customer profile information, prescription item information (e.g., drug types and dosages) associated with each customer profile, stock files from each pharmacy store, and/or a history of prescription item transactions from each pharmacy store.

To provide yet another example, external computing device 114.N may be implemented as any suitable type of computing devices to facilitate user interaction with central hosting service 114. In such a case, external computing device 114.N may receive user input defining rule parameters or other communications from user 115. As further discussed below, these rule parameters may form the overall rule processing to facilitate automatic stock tracking, ordering, and replenishment of dispensed prescription item stock, as further discussed herein. In an embodiment, upon the rule parameters triggering stock replenishment, one or more external computing devices 114.1-114.N may generate a purchase order and transmit or otherwise communicate the purchase order to a suitable party for fulfillment (e.g., to computing device 105).

Furthermore, because one or more computing devices 104.1-104.M may communicate with external computing devices 114.1-114.N, users 102.1-102.M may view a prescription item's current availability (e.g., whether a prescription item is in stock or out of stock) and use this information to plan ahead when ordering new stock and/or when establishing the various rules to facilitate automated stock tracking, ordering, and replenishment, as further discussed herein. Additionally or alternatively, the one or more computing devices 104.1-104.M may allow drugs to de dispensed from each pharmacy location in the event of a network outage, power failure, etc., and thus may be configured to operate in an offline mode.

In various embodiments, one or more external computing devices 114.1-114.N may store and/or access secure data that is of a private, proprietary, and/or sensitive nature. As a result, various embodiments of one or more external computing devices 114.1-114.N, communication network 112, and/or one or more computing devices 104.1-104.M may implement appropriate security protocols such as encryption, secure links, network authentication, firewalls, etc., to appropriately protect and secure such data.

Again, database 114.3 may be configured to store any suitable relevant data as described in the embodiments presented herein related to the operation of exemplary prescription item stock management system 100. Such data might include, for example, customer profile information, payment information, customer prescription information, prescription item information such as a prescription drug brand, type, and/or dosage, a time and date when each prescription item was dispensed by each pharmacy and to which customer, a history of prescribed prescription item transactions, a history of orders placed for additional prescription items, etc. To provide additional examples, data stored in database 114.3 may include stock and/or inventory files or other information, stock keeping units (SKUs), price information, store information such as store locations, store numbers, etc. One or more of external computing devices 114.1-114.N may communicate with database 114.3 to store data to and/or read data from database 114.3 as needed to facilitate the appropriate functions of the embodiments as described herein.

The various embodiments described herein relate to generating, storing, and analyzing (e.g., via one or more of external computing devices 114.1-114.N) prescription item transaction data from one or more pharmacies to facilitate automatic stock tracking, ordering, and replenishment. The transaction data may include any suitable level of granularity based upon the desired inventory accuracy and/or the specific conditions in which purchase orders should be generated. For example, the prescription item transaction data may include not only whether a particular prescription was filled, but whether the prescription was completely filled, the number of prescription items (e.g., dosage units, pills, capsules, etc.) that were dispensed, whether the prescription order was partially filled (e.g., an "owings" exists) due to the amount of a received order or stock on hand not allowing a prescription order to be completely filled when it is picked up. As will be further discussed below, any portion of the transaction data may be used to trigger the generation and transmission of a purchase order for a particular pharmacy store, which may be in addition to or instead of purchase orders that are generated as a result of the minimum stocked number of prescription items falling below a threshold number.

Each of the one or more computing devices 104.1-104.M may be located in or otherwise associated with a pharmacy or other retail store that dispenses prescription items, such as prescription drugs. Therefore, each store may maintain a record of internal physical drug inventory at that particular pharmacy store, but transmit the store's actual stock files (e.g., stocking information, a history of transactions, etc.) to central hosting service 114. Thus, once a prescription item stock has been depleted to some minimum threshold stocked number, a purchase order may be generated via central hosting service 114 to reorder the prescription item stock, thereby replenishing the prescription item stock up to a maximum stocked number. As additional prescriptions are dispensed, this process may be repeated for each pharmacy store, thereby ensuring that ample prescription item stock is on hand at each pharmacy location to meet their respective demands.

Embodiments described herein facilitate the tracking of prescription item stock and generating purchase orders to replenish depleted stock. For some types of prescription orders, known as "due date" prescription orders, the prescription stock is ordered from the manufacturer or a third party prescription delivery company on a one-for-one basis to be delivered on an agreed upon date, which is typically delivered close to when the prescription will be dispensed to the patient, as the delivery of due date prescriptions may be triggered upon prescriptions being processed and transmitted by a pharmacy location user. Due date prescription orders typically apply to those that are dispensed to patients with chronic ailments, for example. These types of prescription orders lend themselves well to advance ordering practices as there is a regular and consistent demand for such drugs, which allows their stock to be depleted and re-ordered in a somewhat predictable manner.

In contrast to due date prescription orders, due now prescription orders are those in which a pharmacy needs dispensed from its stock holding immediately. For example, a patient may visit their physician, have a prescription submitted and filled by the pharmacy, and then pick up the filled prescription order all in the same day. Due now prescription orders, therefore, tend to vary more in their demand, which traditionally requires the pharmacy to examine their stocked inventory more often to determine when a purchase order should be submitted.

Therefore, embodiments of exemplary prescription item stock management system 100 as described throughout the present disclosure are particularly well-suited to tracking due now prescription orders. To do so, each pharmacy location may transmit or otherwise communicate its stocking data to central hosting service 114.

For example, as prescription item orders are received, filled, dispensed, and/or as new orders are placed, one or more users 102.1-102.M may enter these details into their respective computing devices 104.1-104.M through a suitable user interface executed thereon. Additionally or alternatively, the stock files may be automatically updated at central hosting service 114, transmitted to central hosting service 114, and/or modified at central hosting service 114 based upon various actions taken by one or more users 102.1-102.M. For example, the stock file stored at central hosting service 114 may automatically be adjusted when a user completes prescription data entry, when a prescription item transaction (e.g., payment) is processed, etc. One or more users 102.1-102.M may also subsequently manually adjust the stock files stored via central hosting service 114 via their respective computing devices 104.1-104.M, for example, to account for various inconsistencies, damaged items, when a prescription item has expired and needs to be disposed, etc.

In any event, each pharmacy may transmit their stock file data to central hosting service 114. The stock file may indicate various details of the history of dispensed prescription items and their current in-store prescription item inventory. This stock file may be stored, for example, on one or more external computing devices 114.1-114.N, where one or more computing devices 104.1-104.M may access the stock file data. In an embodiment, one or more external computing devices 114.1-114.N may store the stock files for an aggregation of any suitable number of pharmacies. Furthermore, embodiments include one or more external computing devices 114.1-114.N generating one or more rules, which may be specified based upon various metrics obtained via an analysis of any number of the transmitted pharmacy stock files. As discussed in further detail below, the rules may be based upon the history, cost, and frequency of dispensed prescription items at a particular pharmacy or a group of pharmacies. These rules may determine, for example, which prescription items qualify for automatic stock tracking and replenishment, a minimum and maximum stocked number to maintain on hand for each prescription item dispensed by a pharmacy, external factors that may override or adjust these rules, etc.

In an embodiment, the rules generated for each prescription item stocked at one or more pharmacy locations may be used to trigger the generation of a purchase order via central hosting service 114. The rules may specify when the purchase order should be generated via central hosting service 114 (e.g., when a prescription item stock falls below a calculated minimum stocked number) as well as how much prescription item stock to order (e.g., to bring the in house stock up to the maximum stocked number). These purchase orders may be generated via central hosting service 114 and sent to the manufacturer, delivery service, warehouse, or other third party (e.g. computing device 105) in accordance with any suitable techniques.

For example, one or more of external computing devices 114.1-114.N may generate an electronic purchase order that is transmitted to a delivery service (e.g. computing device 105) in the form of an electronic message, notifying the delivery service of the details of the prescription item order. To provide another example, one or more of external computing devices 114.1-114.N may generate and transmit a facsimile to the appropriate party (e.g. computing device 105) with the details of the prescription item order, generate and place an automated phone call (e.g., to user 103), generate and send an automated mailing, receive a notification to place an order, etc. To provide another example, user 115 (e.g., a support office control) may manually generate and/or place purchase orders using any suitable means of communication, such as electronic message transmission, phone calls, facsimile, etc.

Figure 2:
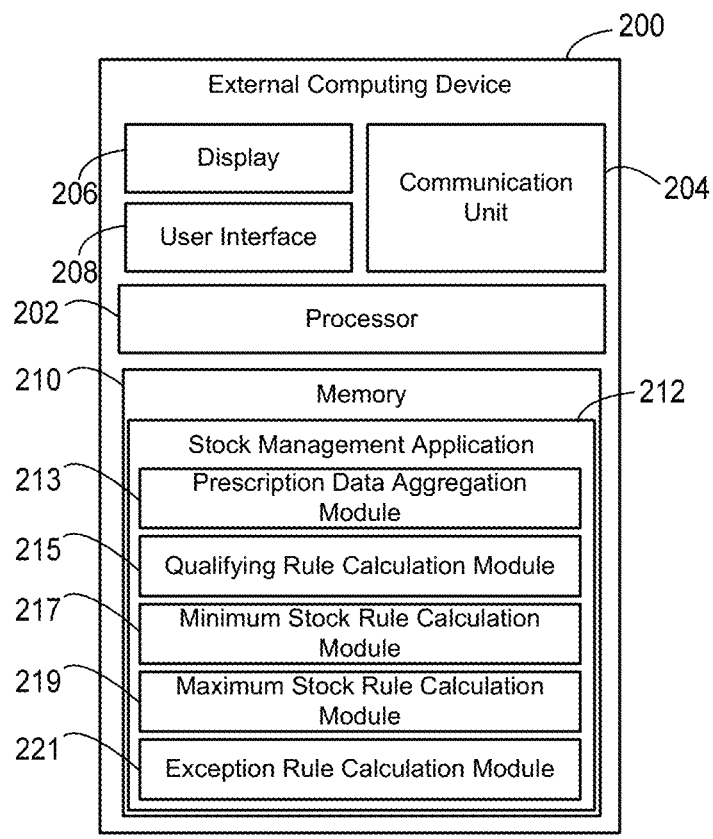
FIG. 2 illustrates a block diagram of an exemplary external computing device 200 in accordance with an exemplary embodiment of the present disclosure.

FIG. 2 illustrates a block diagram of an exemplary external computing device 200 in accordance with an exemplary embodiment of the present disclosure. In an embodiment, external computing device 200 may be an implementation of one or more external computing devices 114.1-114.N, for example, as shown in FIG. 2. External computing device 200 may include a processor 202, a communication unit 204, a display 206, a user interface 208, and a memory 210. Although the embodiments are described herein as functioning on a single external computing device 200 for simplicity, embodiments also include the execution of various logical layers, the use of processing resources, memory, the execution of application data, etc., that is distributed among any suitable number of external computing devices 114.1-114.N that constitute central hosting service 114.

Processor 202 may be implemented as any suitable type and/or number of processors, such as a host processor for the relevant device in which external computing device 200 is implemented, for example. Processor 202 may be configured to communicate with one or more of communication unit 204, display 206, user interface 208, and/or memory 210 to send data to and/or receive data from these components.

Communication unit 204 may be configured to enable data communications between external computing device 200 and one or more other devices, such as one or more computing devices 104.1-104.M, for example, as shown in FIG. 1. In an embodiment, communication unit 204 may be configured to receive data, such as prescription item transaction data, stock information, stock files, etc., from one or more computing devices. In an embodiment, external computing device 200 may be configured to send data, including stock file information received from another computing device, for example, to another computing device, such as one or more computing devices 104.1-104.M and/or one or more external computing devices 114.1-114.N, as shown in FIG. 1.

Communication unit 204 may be implemented with any combination of suitable hardware and/or software to enable these functions. For example, communication unit 204 may be implemented with any suitable number of wired and/or wireless transceivers, network interfaces, physical layers (PHY), ports, antennas, etc. In embodiments in which communication device 204 is an external computing device, communication unit 204 may enable communications between other external computing devices (e.g., one or more of external computing devices 114.1-114.N, as shown in FIG. 1), one or more networks (e.g., communication network 112, as shown in FIG. 1) and/or one or more pharmacy computing devices (e.g., one or more of computing devices 104.1-104.M, as shown in FIG. 1).

Display 206 may be implemented as any suitable type of display and may facilitate user interaction with external computing device 200 in conjunction with user interface 208. For example, display 206 may be implemented as a capacitive touch screen display, a resistive touch screen display, etc. In various embodiments, display 206 may be configured to work in conjunction with processor 202 and/or communication unit 204 to display purchase orders for prescription items, to display details associated with prescription stock files, etc.

User interface 208 may be configured to allow a user to interact with external computing device 200. For example, user interface 208 may include a user-input device such as an interactive portion of display 206 (e.g., a "soft" keyboard displayed on display 206), an external hardware keyboard configured to communicate with external computing device 200 via a wired or a wireless connection, one or more keyboards, keypads, an external mouse, or any other suitable user-input device.

In embodiments in which external computing device 200 is implemented as part of a device that performs automated tasks and/or does not otherwise require user input (e.g., a web server or other type of server), display 206 and/or user interface 208 may not be needed and thus may be omitted.

When communicating with memory 210, processor 202 may be configured to store to and/or read data from memory 210. In some aspects, processor 202 may be configured to communicate with additional data storage mechanisms that are not shown in FIG. 2 for purposes of brevity (e.g., one or more hard disk drives, optical storage drives, solid state storage devices, databases, etc.) that reside within, are associated with external computing device 200, and/or are accessible via communication unit 204.

In accordance with various embodiments, memory 210 may be a computer-readable non-transitory storage device that may include any combination of volatile (e.g., a random access memory (RAM), or a non-volatile memory (e.g., battery-backed RAM, FLASH, etc.)). Memory 210 may be configured to store instructions executable on processor 202. These instructions may include machine readable instructions that, when executed by processor 202, cause processor 202 to perform various acts.

Memory 210 may include a stock management application 212 and one or more memory modules utilized by stock management application 212 such as a prescription data aggregation module 213, a qualifying rule calculation module 215, a minimum stock rule calculation module 217, a maximum stock rule calculation module 219, and an exception rule calculation module 221. Stock management application 212 may, when executed by processor 202, work in conjunction with one or more of these modules, communication unit 204, display 206, and/or user interface 208 to perform one or more functions of the aspects as described herein.

Stock management application 212 may include instructions that, when executed by processor 202, facilitate the implementation of a web-based and/or network-based application platform. This application platform may be utilized, for example, in conjunction with a retailer and/or pharmacy infrastructure to support interactions between one or more pharmacy computing devices (e.g., one or more computing devices 104.1-104.M) and/or one or more other external computing devices (e.g., one or more external computing devices 114.1-114.N). This application platform may also be configured to apply rule parameters selected by a user at a pharmacy location to specific prescription items prescribed at that pharmacy location, which may be based on, for example, an analysis of prescription item transactions for the same pharmacy location or an aggregation of several pharmacy locations. The rule parameters may provide the framework for various rules that may specify, for example, which prescription items qualify for automatic stock tracking, ordering, and replenishment, and the minimum and maximum stocked numbers associated with qualifying prescription items. The selection, application, and implementation of these rule parameters are further discussed below with reference to FIGS. 4A-4D.

Prescription data aggregation module 213 is a portion of memory 206 configured to store instructions, that when executed by processor 202, cause processor 202 to receive prescription transaction data from one or more pharmacy computers, to associate these prescription item transactions with a particular store's file, and to update the store's stock file. For example, referring back to FIG. 1, user 102.1 may interact with computing device 104.1 to manually update prescription item inventory. To provide another example, computing device 104.1 may perform various stock-updating automated procedures that result in updates to the stock file for the pharmacy associated with computing device 104.1. In either case, embodiments include processor 202 executing instructions stored in prescription data aggregation module 213 to receive the updated data, to associate the updated data with a particular pharmacy or store (e.g., a store number) and to update the stock file for the store associated with the updated data.

Again, external computing device 200 may store one or more stock files locally (e.g., in a suitable portion of memory 206) or on one or more external computing devices such as external computing devices 114.1-114.N. Embodiments include processor 202 executing instructions stored in prescription data aggregation module 213 to update the data at any of these locations where the stock files may be stored.

In an embodiment, processor 202 may execute instructions stored in prescription data aggregation module 213 to organize stock files and/or prescription item transactions in any suitable manner such that the data may be provided to users via each pharmacy location's respective computing device. Referring back to FIG. 1 as an example, user 115 (e.g., a support office control) may interact with one or more external computing devices 114.1-114.N to specify various rule parameters for prescription items stocked by that particular pharmacy. To do so, one or more external computing devices 114.1-114.N may need to access prescription item transactions over a specified sampling period (e.g., the last month, 6 months, a year, etc.). Thus, embodiments include processor 202 executing instructions stored in prescription data aggregation module 213 to not only aggregate and store the prescription item transactional data and/or stock files from several prescription stores, but to format this data and/or make this data available to one or more other external computing devices 114.1-114.N, such that rules may be generated using this data to facilitate automatic stock tracking, ordering, and replenishment.

Qualifying rule calculation module 215 is a portion of memory 206 configured to store instructions, that when executed by processor 202, cause processor 202 to identify various conditions that, upon being satisfied, result in a prescription item qualifying for automatic stock tracking, ordering, and replenishment. In an embodiment, processor 202 may execute instructions stored in qualifying rule calculation module 215 to generate rules that may be applied to each prescription item in a pharmacy's inventory using the history of prescription item transactions.

For example, a pharmacy may maintain stock for several prescription items, but only choose to track and automatically replenish a subset of those prescription items. Although daily dispensing frequencies may vary throughout a sampling period, various statistical analyses may be applied to the prescribed prescription item transactions to derive various metrics in an attempt to forecast future demand, set the appropriate triggers to order additional prescription item stock, and/or set a minimum and a maximum stocked number to guide the ordering process.

An example of a parameter used in the formulation of a rule may include a range of one or more metrics that may derived from a statistical analysis of prescription item transactions, such as average daily dispensing frequency values over a sampling period, for example. The sampling period may be specified by a user or be a default sampling period, which is further discussed below with reference to FIGS. 4A-4D. That is, it is desirable for a pharmacy to automatically track, order, and replenish stock for prescription items that are dispensed at a higher average daily frequency compared to other prescription items, as doing so creates less risk of prescription items being of overstocked.

Another example of a parameter used in the formulation of a rule may include a range of costs of prescribed items. It is more desirable for a pharmacy to automatically track and replenish stock for prescription items that are cheaper because, if extra stock is ordered and needs to be disposed, the pharmacy absorbs less of a financial burden in doing so. Embodiments include processor 202 executing instructions stored in qualifying rule calculation module 215 to facilitate a user specifying any suitable range, combination, and/or weighting of various parameters to determine which stocked items may qualify for automatic stock tracking and replenishment. The generation and application of qualifying rules are further discussed below with reference to FIG. 4A.

Minimum stock rule calculation module 217 is a portion of memory 206 configured to store instructions, that when executed by processor 202, cause processor 202 to calculate a rule for the minimum stocked number to maintain on hand for a particular qualifying prescription item. In other words, once a prescription item qualifies for automated stock tracking, ordering, and replenishment, as discussed above with reference to qualifying rule calculation module 215, a user may further specify, based upon various parameters calculated from a statistical analysis of that prescribed prescription item's transactions, the minimum stocked number to maintain on hand for that prescription item. In some embodiments, the minimum stocked number may act as a trigger, for example, upon which to generate and transmit a purchase order, such that once the prescription item's stock falls below the minimum number, the purchase order is automatically, semi-automatically, or manually generated.

But in other embodiments, it may be desirable to "overstock" certain prescription items, based upon demand, for example. In embodiments in which a prescription drug item is overstocked, execution of minimum stock rule calculation module 217 via processor 202 may compensate for any overstock by reducing the minimum stocked number such that stock ordering is deferred to reduce the overstock. Thus, embodiments include the calculation of an adjusted minimum stocked number based upon a particular prescription item being overstocked by reducing the minimum stocked number that would otherwise be applicable if the prescription item was not overstocked. The adjusted minimum stocked number may be calculated, for example, based upon a proportion of the overstock, the amount of overstock, etc.

Again, the average daily dispensing frequency value of a prescribed item may be used as part of the determination of whether particular prescribed items qualify for automatic stock tracking, ordering, and replenishment. In addition, the average daily dispensing frequency value (or a multiple thereof) may likewise be used to calculate the minimum stocked number. That is, if the sampling period is 30 days, the average daily dispensing frequency value would be calculated by dividing the total prescriptions dispensed over the 30 day interval for a particular qualifying prescription item by 30. The average daily dispensing frequency value or a multiple thereof (2 times this number would yield the anticipated number of prescriptions to be dispensed over two days in the sampling period) may be used to calculate the minimum stocked number.

To provide another example, a maximum average daily dispensing frequency value over the sampling period may be calculated and used as the basis for calculating the minimum stocked number. For example, if the sampling period is 30 days, a user may specify that only a subset of the total prescriptions dispensed over the 30 day interval should be averaged as opposed to the entire sampling period. In other words, if a user specifies that the 10 highest daily dispensing frequency values within the 30 day sampling period are to be used, processor 202 may calculate the maximum average daily dispensing frequency value by summing the total prescriptions dispensed over the ten days and dividing this number by 10.

To provide an illustrative example of a maximum average daily dispensing frequency value calculation, dispensing frequency values over an 11 day period may include the following values: 10, 10, 10, 10, 17, 17, 17, 17, 20, 20, and 20. Selecting the top 'x' highest daily dispensing frequencies, whereby x=4, specifies the 4 highest daily dispensing frequency values, thereby selecting values of 20, 20, 20, and 17 from the 11 day sampling period, and averaging these would yield a maximum average daily dispensing frequency value of 19.25. In the event that a user specifies a number 'x' of the highest daily dispensing frequency values that exceeds the available number of daily dispensing frequency values, embodiments include the maximum average daily dispensing frequency value calculation being performed by iteratively reducing x by 1 until the calculation can be made. Using the previous example, if a user specified x=12, because only 11 days of frequency values are available based upon the sampling period that has been selected, embodiments include x being instead set to 11 (and then 10, 9, 8, etc., as needed based upon the sampling period) until x is equal to at least the same number of days in the selected sampling period (in this case 11), to calculate the maximum average daily dispensing frequency value.

To provide another example, a maximum daily dispensing frequency value may be calculated and used as the basis for calculating the minimum stocked number, which may utilize the same or similar dispensing frequency values over a specified period as part of the calculation. For example, a user may specify a number of 'x' occurrences within the sampling period to be averaged (e.g., a number of daily dispensing frequency values, such as 4), a tolerance from which these same values may deviate from one another (e.g., 10%), and a sampling period over which to analyze dispensing frequency values (e.g., 30 days). To calculate the maximum daily dispensing frequency value, embodiments include processor 202 finding the four top daily dispensing frequency values within the month that are within 10% of one another. Once these four daily dispensing frequency values are identified, processor 202 may calculate the maximum daily dispensing frequency value by averaging them.

To provide an illustrative example, embodiments include processor 202 first reducing the number of occurrences to be considered using the appropriate tolerance and then applying the specified logic to match the number of occurrences. Thus, for 'x'=4, a tolerance=10%, and values of 51, 52, 53, and 97, the number of occurrences would be reduced to 3, because only three values exist within the 10% tolerance of one another (51, 52, and 53), and therefore the selected values would be 51, 52, and 53. Continuing this example, calculating the maximum daily dispensing frequency value from these three values would result in a maximum daily dispensing frequency value of 52.

In an embodiment, the maximum daily dispensing frequency value may be calculated in an iterative manner such that the data is analyzed until a number of occurrences is found (either an exact match or within the specified tolerance). To provide another illustrative example, if x=5, the specified tolerance=15%, and the daily dispensing frequency values are 100 and 224, then the number of occurrences is 1 and the selected value is 224, because there are no occurrences within 15% of each other.

To provide yet another illustrative example of a maximum daily dispensing frequency value calculation, if x=4, the tolerance=15%, and the values are 10, 10, 10, 10, 17, 17, 17, 17, 20, 20, and 20, then the number of occurrences should be 4 and the selected values should be 20, 20, 20, 17, resulting in the maximum daily dispensing frequency value of (20+20+20+17)/4=19.25.

Embodiments include processor 202 executing instructions stored in minimum stock rule calculation module 217 to facilitate a user specifying any suitable number and/or type of rule parameters upon which to calculate of the minimum stocked number. For example, a user may specify rule parameters that calculate the minimum stocked number as the greater of any combination of (1) the average daily dispensing frequency value over a sampling period (or a multiple thereof), (2) a maximum average daily dispensing frequency value, and/or (3) the maximum daily dispensing frequency value. The generation and application of rules that specify the minimum stocked number of a qualifying prescription item to keep on hand before ordering more are further discussed below with reference to FIG. 4B.

Maximum stock rule calculation module 219 is a portion of memory 206 configured to store instructions, that when executed by processor 202, cause processor 202 to calculate a maximum stocked number to maintain on hand for a qualifying prescription item. This maximum stocked number may be used, for example, as a guide when the purchase order is generated and transmitted to replenish depleted stock. For example, the purchase order may order an amount of prescription item stock that is the difference between the minimum stocked number (or less if, when generated, there is less than the minimum stocked number available) and the maximum stocked number.

In various embodiments, processor 202 may calculate the maximum stocked number using any suitable number and/or type of metrics derived from the analysis of the prescribed prescription item transactions, such as any of those discussed above that are used to calculate the minimum stocked number, for example.

For example, a number of days of stock cover may be calculated based upon a multiple of the average daily dispensing frequency value over a specified sampling period, which may be the same average daily dispensing frequency value that is used in the calculation of the minimum stocked number. To provide an illustrative example, if 2 days of stock cover are used as the basis of the maximum stocked number calculation, then the maximum stocked number may be calculated by multiplying the average day quantity by the number of days stock cover, then adding the minimum stock value, as shown in Eqn. 1 below:

$$\text{Maximum Stocked Number} = [(\text{Average daily dispensing frequency value} \times 2) + \text{the minimum stocked number}]. \quad \text{Eqn. 1:}$$

The generation and application of rules that specify the maximum stocked number of a qualifying prescription item to keep on hand are further discussed below with reference to FIG. 4C.

Exception rule calculation module 221 may be a portion of memory 206 configured to store instructions, that when executed by processor 202, cause processor 202 to apply various user-specified rule parameters, which may be applied to the aforementioned qualifying rules or used to additionally or alternatively specify conditions that result in an order being placed, regardless of whether a particular stocked prescription item qualifies for automatic stock tracking, ordering, and replenishment. Furthermore, the various user-specified rule parameters may be applied to the minimum stocked calculation rules and/or maximum stocked calculation rules to provide for greater flexibility. For example, a user may specify various factors that are applied to the aforementioned rules to customize their respective outcomes. These factors may take into account a specific pharmacy, a particular region, specific dates in which it may be inaccurate to completely rely on the forecasting resulting from the analysis of prescribed item transactions, etc. The generation and application of these factors are further discussed below with reference to FIG. 4D.

To provide another example, embodiments include other types of prescription order events resulting in the generation of a purchase order to replenish inventory regardless of whether that particular prescription items qualifies for stock tracking. That is, the demand for prescription item inventory may be driven by both prescribed items that are dispensed as well as prescription item orders that are received. To provide an illustrative example, in some instances a partial prescription fill or an owings may be created when on hand prescription item stock is not sufficient to completely fill a prescription order. Therefore, embodiments include the prescription transaction data that is received by external computing device 200 including an indication of any such partial fillings and how much of the prescription item was able to be dispensed.

Instructions in exception rule calculation module 221 may allow a user to specify rule parameters such that that purchase orders are generated and transmitted upon detecting any such partial filings, resulting in the prescription items having an higher demand (which caused the partial filling to occur) to be restocked regardless of whether the prescription item otherwise qualifies for automatic stock tracking and replenishment. However, in the event that a partially filled prescription item does qualify for automatic stock tracking and replenishment, embodiments include exception rule calculation module 221 allowing a user to specify rule parameters that act as an override when partial fillings are detected, causing processor 202 to generate a purchase order as soon the partial filling is detected even if the stocked number for a prescription item qualifying for automatic stock tracking and replenishment has not yet been depleted below the minimum stocked number threshold.

Because external computing device 200 may receive and store prescription item transactions for any suitable number of pharmacies, the statistical analysis of a prescribed prescription item's transactions may be performed over any suitable number of pharmacies, regions, countries, etc. For example, rules may use metrics calculated from an analysis of prescribed prescription item's associated with a single pharmacy or several pharmacies, although the rules may be applied to the transactional data that is associated with prescription item stock at a particular pharmacy location.

In this way, embodiments allow for errors introduced from small samples of prescribed item transactional data to be reduced or eliminated, while providing a user with the flexibility of customizing rule parameters utilizing prescribed prescription item transaction data for a single store if the data is sufficiently accurate.

Figure 3:
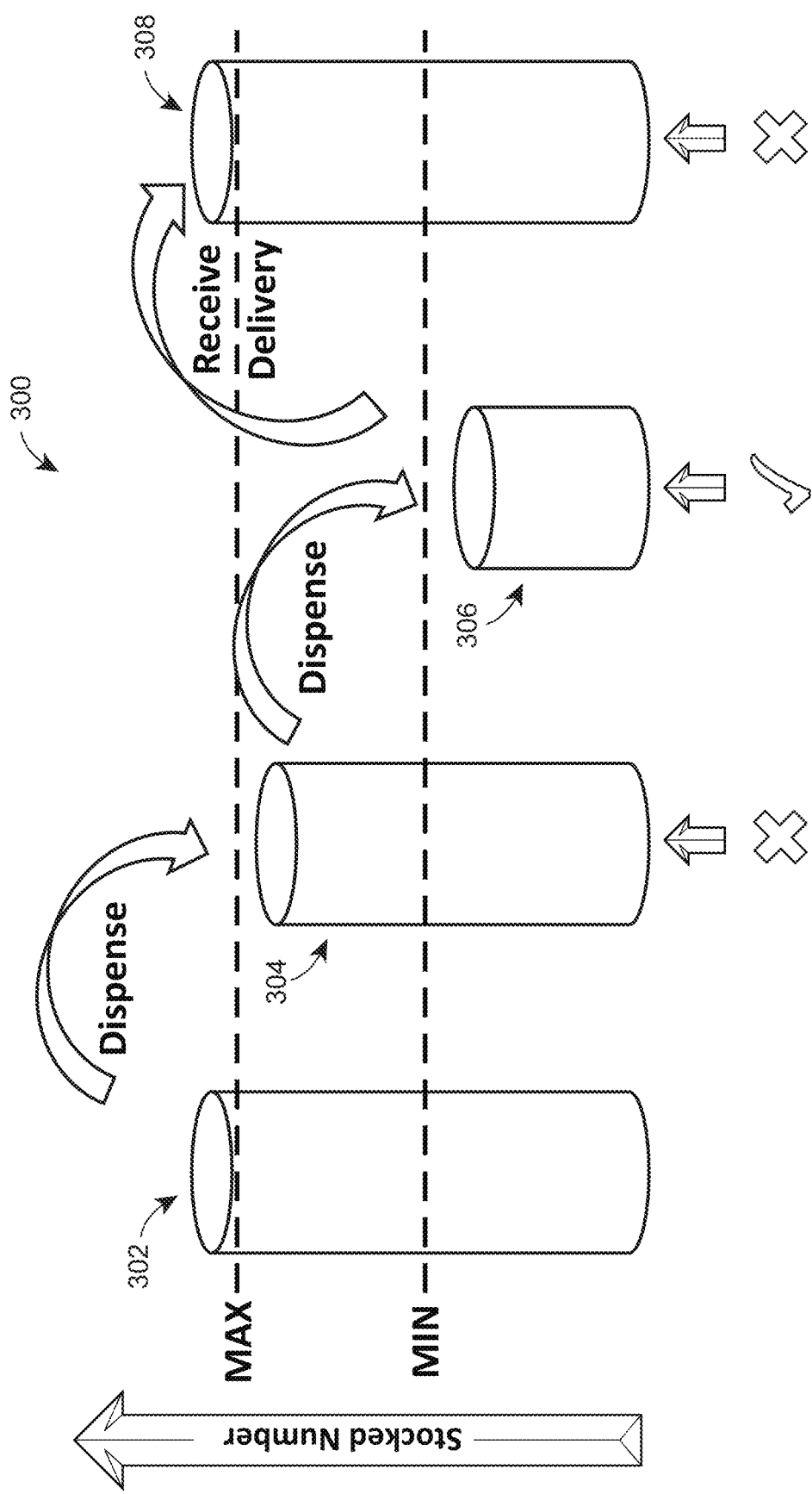
FIG. 3 illustrates an exemplary flow diagram 300 illustrating an overall prescription item dispensing, ordering, and replenishment process in accordance with an exemplary embodiment of the present disclosure.

FIG. 3 illustrates an exemplary flow diagram 300 illustrating an overall prescription item dispensing, ordering, and replenishment process in accordance with an exemplary embodiment of the present disclosure. Flow diagram 300 represents a timeline of the total stocked number of a particular prescription item at various times 302, 304, 306, and 308.

As shown in FIG. 3, time 302 is associated with a time just after new stock is acquired, as the height of the bar at time 302 is equal to the maximum stocked number, which may be calculated for the prescription item as discussed above.

At time 304, some of the prescription item has been dispensed, thereby reducing the overall stocked number from time 302, as shown by the reduced height of the bar at time 304. However, at time 306, the dispensing of the prescription item continues until the stocked number is below the minimum stocked number for the prescription item, which again may be calculated in the various manners discussed above. As a result, a purchase order may be generated and transmitted at time 306, resulting in the prescription item stock being replenished at time 308 by an amount equal to the maximum stocked number upon receiving delivery of the prescription item. This process may repeat over any number of cycles using the minimum and maximum stock number rules as discussed above and elsewhere herein.

Furthermore, because the sampling period specified by each of the aforementioned qualifying rule, minimum stocked number calculation rule, and maximum stocked number rule may be based upon recent sampling periods, the results of the rules being applied to various prescription items may vary over time. For example, a prescription item that qualifies for automatic stock tracking and replenishment using one month of prescribed prescription item transaction data may not do so the next month if the conditions specified by the rule are not met the following month. Similarly, a prescription item that does not qualify for automatic stock tracking and replenishment using one month of prescribed prescription item transaction data may qualify the next month if the conditions specified by the rule are met the following month.

Additionally, the minimum and maximum stock number calculations for a qualifying prescription item may dynamically update over time using the resulting metrics from an analysis of the most recent prescription item transaction data. In this way, embodiments of the automatic stock tracking, ordering, and replenishment system dynamically adapt to accurately anticipate and forecast future demand based upon recent changes in a prescribed item's dispensed rate.

FIG. 4A illustrates an exemplary user interface screen 400 to facilitate the determination of whether a prescription item qualifies for automatic stock tracking in accordance with an exemplary embodiment of the present disclosure. In an embodiment, exemplary user interface screen 400 is an example of what may be displayed on a suitable computing device that is configured to communicate with one or more in-house pharmacy computers. For example, exemplary user interface screen 400 may be displayed on one or more external computing devices 114.1-114.N, as shown in FIG. 1. In such a case, the various rule parameters, which are further discussed below, may be input by an appropriate user, such as user 115, for example, via user interaction with one or more one or more external computing devices 114.1-114.N.

In an embodiment, the various user inputs and rule parameters as discussed herein with reference to FIGS.

4A-4D may be communicated from an in-house pharmacy computing device to one or more back-end and/or external computing devices, such as external computing devices 114.1-114.N, for example, as shown in FIG. 1. In an embodiment, the application shown throughout FIGS. 4A-4D may be supported via processor 202 executing one or more instructions and/or modules stored in memory 210, such as the execution of stock management application 212, for example, as shown in FIG. 2. Furthermore, embodiments include the overall rule parameters, which specify how the resulting decisions for each rule are determined, being stored on the one or more back-end and/or external computing devices while allowing users to access and view this data via their respective in-house pharmacy computers.

As shown in FIG. 4A, exemplary user interface 400 includes a tabbed grid layout with tabs 402, 404, 406, and 408. As shown in FIG. 4A, exemplary user interface 400 corresponds to a view that is displayed upon a user selecting tab 402, which allows a user to specify various rule parameters. In this case, the rule parameters result in a determination of which prescribed items qualify for automatic stock tracking, ordering, and replenishment.

Exemplary user interface 400 also includes several interactive portions as well as other portions that provide feedback to the user, such as a grid association interactive button 409, a grid code field 410, a grid structure interactive button 411, a grid name interactive field 412, an interactive cell options field 413, a number of stores field 414, a grid 415, an interactive comments field 416, an interactive grid description field 418, and an update comments field 419.

As will be further discussed below with reference to FIGS. 4B-4D, some portions of exemplary user interface 400 may remain the same as a user selects different tabs 402, 404, 406, and 408, while other portions of exemplary user interface 400 may change to facilitate additional or alternate functions.

Figure 4B:
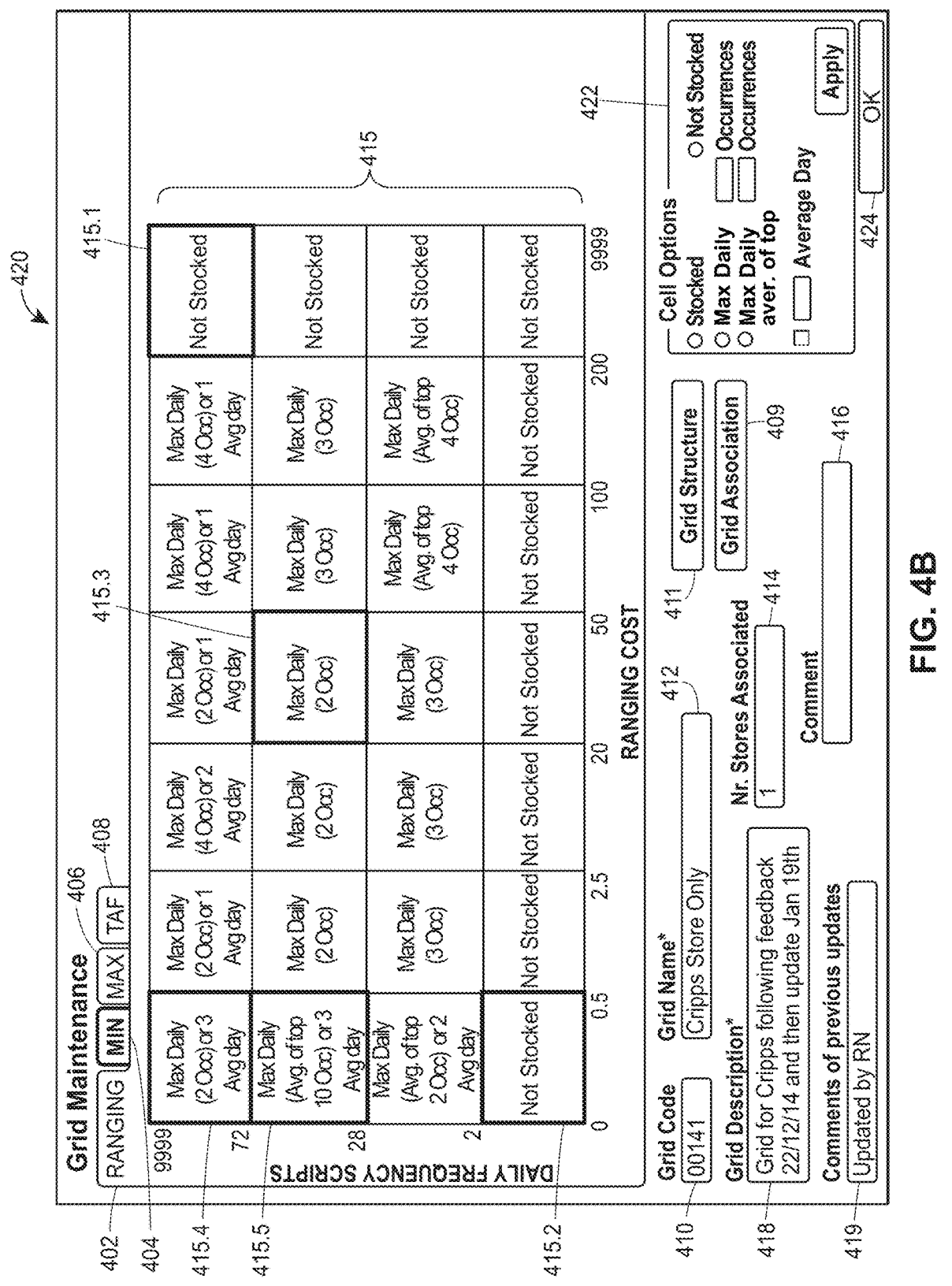

The grid shown in FIG. 4A is applicable to the prescription item transactions for a single store over a specified sampling period. However, a user may specify any suitable number of stores by selecting grid association interactive button 409, which may prompt a user to select specific stores to associate with the grid rules. Upon selecting a number of stores for which the grid rule applies, the selection may be displayed as feedback in the number of stores field 414. In an embodiment, the grids shown in FIGS. 4A-4D may function as a single "global" grid for a number of pharmacy stores, such as all stored over which stock data is collected, for example.

A user may also name the rule via grid name interactive field 412 and add comments in interactive comments field 416, as shown in FIG. 4A. Upon a user adding comments to interactive comments field 416, these comments may be indicated in the updated comments field 419 when the rule is later accessed or otherwise subsequently opened.

As further discussed below, the various parameters used for the rule shown in FIG. 4A may utilize prescription item transaction data for one or more selected pharmacies or stores. The prescription item transaction data may be based upon any suitable sampling time period, such as the last 30 days of transactions, for example. In some embodiments, this sampling period may be a predetermined or default period. But in other embodiments, this sampling period may be specified by a user, for example.

Embodiments include users generating different rules for each different pharmacy or store, which may each include different parameters, sampling periods, and/or different store selections. In accordance with such embodiments, users may uniquely name their rules in any suitable manner, which may be identified by grid code field 410, for example. As users update their rules to include different stores, different sampling periods, and/or to specify different parameters, users may maintain a log of tracked changes using interactive grid description field 418. By saving user comments with each rule, different users may adjust the same rule that is used for a single pharmacy location in a manner that conveys the types of changes and when these changes were made to other users as each rule is accessed.

Again, exemplary user interface 400 includes a grid 415, which may be of any suitable size. As shown in FIG. 4A, grid 415 has a vertical axis labeled "daily frequency scripts," and a horizontal axis labeled "ranging cost." In this example, the rule parameters are the result of the intersection of the ranges defined by the vertical axis grid cells and the horizontal axis grid cells, which represent average daily frequency prescriptions and cost, respectively. However, any suitable type of metrics may be used to define the rule parameters such that a determination may be accurately made regarding which of the prescription items qualifies for automatic stock tracking, ordering, and replenishment.

Using the example shown in FIG. 4A, the vertical axis indicates a number daily frequency prescriptions, or average daily dispensing frequency values, that increase from zero per day to some maximum number, which is shown in FIG. 4A as "9999," but may be any suitable frequency value. For example, a pharmacy may dispense several products over a sampling period at different numbers per day, resulting in each prescribed item falling into one of the ranges as indicated by the tick marks on the vertical axis of grid 415. In an embodiment, a user may adjust these tick marks, and thus the ranges of each average daily dispensing frequency value associated with the vertical axis of grid 415. For example, a user may select grid structure interactive button 411 to specify the minimum average daily dispensing frequency value, the maximum average daily dispensing frequency value, the number of vertical grid cells, and/or the ranges associated with each of the vertical grid cells. In this way, a user may tailor the grid based upon a store's specific prescription item transactions to vary the granularity of ranges as desired.

Continuing to reference FIG. 4B, the horizontal axis indicates a cost that increases from zero to some maximum number, which is shown in FIG. 4A as "9999" but may be any suitable cost value. For example, a pharmacy may dispense several products over a sampling period that have different costs, resulting in each prescribed item falling into one of the ranges as indicated by the tick marks on the horizontal axis of grid 415. In an embodiment, a user may adjust these tick marks, and thus the ranges of costs associated with the horizontal axis of grid 415. For example, a user may select grid structure interactive button 411 to specify the minimum cost, the maximum cost, the number of horizontal grid cells, and/or the ranges associated with each of the horizontal grid cells, thereby providing additional customization based upon a store's specific prescription item transactions.

In various embodiments, any suitable cost metric may be used that adequately conveys the need to automatically track, order, and replenish stock of a particular prescription item For example, the cost may be the cost of a prescribed unit of a particular prescription drug (e.g., a single dosage) a prepackaged unit of several doses, a minimum packaged number of doses, a number of packs, an optimum and/or preferred pack size, etc. Embodiments also include a user specifying the type of cost, the type of currency used, etc. In this way, embodiments allow the stock tracking and replenishment techniques discussed herein to be applicable regardless of local currency and/or customs.

To define which prescription items qualify for automatic stock tracking, ordering, and replenishment, a user may utilize interactive cell options field 413 to apply the rule for prescription items that fall within the ranges defined by particular grid cells within grid 415. For example, a user may select grid cell 415.1 and specify this cell option as "no" using interactive cell options field 413. As a result, prescription items that are dispensed at an average daily dispensing frequency above 72 per day, and also have a cost above $200 per unit, will not qualify for automatic stock tracking and replenishment. Similarly, a user may select grid cell 415.2 to specify that prescription items that are dispensed at an average daily dispensing frequency below 2 per day, and also have a cost below $0.50 per unit, will not qualify for automatic stock tracking, ordering, and replenishment.

To provide additional examples, a user may select grid cell 415.3 to specify that prescription items that are dispensed at an average daily dispensing frequency between 28 and 72 per day, and also have a cost between $20-$50 per unit, will qualify for automatic stock tracking, ordering, and replenishment. Furthermore, a user may select grid cell 415.4 to specify that prescription items that are dispensed at an average daily dispensing frequency above 72 per day, and also have a cost less than $0.50 per unit, will qualify for automatic stock tracking, ordering, and replenishment. Finally, a user may select grid cell 415.5 to specify that prescription items that are dispensed at an average daily dispensing frequency between 28 and 72 per day, and also have a cost less than $0.50 per unit, will qualify for automatic stock tracking, ordering, and replenishment.

A user may repeat this process to assign "yes," "no," or "excluded" status to each grid cell within grid 415. While the assignment of yes and no to specific grid cells may represent whether stock tracking and replenishment is performed for stocked prescription items meeting each respective cell's frequency and cost ranges, a cell may be set to "exclude" to specify that automatic stock tracking and replenishment calculations are not required for a period of time for prescription stock items associated with a respective cell's frequency and cost ranges, and the daily frequency ranging values will not be re-calculated during the next elaboration; previously calculated values will be considered instead.

In this way, a complete set of rule parameters is established for an entire pharmacy's stock. Once the rule is established, any prescription items in stock meeting the average daily dispensing frequency value and cost ranges will qualify for automatic stock tracking, ordering, and replenishment. The user interface may then be further utilized to specify, for those prescription items that do qualify for automatic stock tracking, ordering, and replenishment, additional parameters to specify the minimum stock number that triggers a purchase order being generated and transmitted to replenish the depleted stock. This is further discussed below with reference to FIG. 4B.

FIG. 4B illustrates an exemplary user interface screen 420 to facilitate the calculation of a minimum stocked number for a qualifying prescription item in accordance with an exemplary embodiment of the present disclosure. In an embodiment, exemplary user interface screen 420 corresponds to a transition from another exemplary user interface screen 400, 440, or 460 due to a user selecting tab 404 while in the other exemplary user interface screen. As discussed above, exemplary user interface 420 shares several portions with other exemplary user interfaces. For example, grid association interactive button 409, grid code field 410, grid structure interactive button 411, grid name interactive field 412, number of stores field 414, interactive comments field 416, interactive grid description field 418, and update comments field 419 are also displayed in exemplary user interface 420. These portions may perform the same functions as discussed above with reference to FIG. 4A.

However, exemplary user interface 420 also includes an interactive cell options field 422, which a user may be utilized to set the various rule parameters for each prescription item in grid 415 that qualifies for automatic stock tracking and replenishment. For example, referring back to FIG. 4A, exemplary user interface 400 included grid 415, which indicated the ranges of metrics for various prescription items that, when met, would qualify those prescription items for automatic stock tracking, ordering, and replenishment.

These same qualifying grid cells are shown in grid 415, as shown in FIG. 4B. That is, grid cells 415.1 and 415.2 are now labeled "not stocked," while grid cells 415.3-415.5 have a selected minimum stock calculation rule applied to these cells. Any suitable metrics based upon an analysis of prescription item transaction data may be used for the calculation of the minimum stocked number, and are not limited to the examples discussed herein.

For example, interactive cell options field 422 provides a user with the option to select one of the grid cells within grid 415 and to identify that grid cell as either "stocked" or "not stocked." In an embodiment, grid cells that do not qualify for automatic stock tracking and replenishment may be set to "not stocked" by default. Upon selecting the stocked option, a user may select one or more ways in which the minimum stocked number for the prescription item is calculated and select interactive "ok" button 424 to apply these selections to an individual grid cell. In an embodiment, two or more options may be selected, with the greater number of these calculations yielding the minimum stocked number for the particular prescription items that fall within the ranges defined by each of the grid cells within grid 415.

For example, a user may define the minimum stocked number as a number of prescription items dispensed over a number of at a rate of the average daily dispensing frequency value over a sampling period. This sampling period may be, for example, the same sampling period defined for the calculation of the average daily dispensing frequency values used to determine which prescription items qualify for automatic stock tracking and replenishment, as discussed above with reference to FIG. 4A. For example, a user may select a grid cell within grid 415, select the check box in interactive cell options field 422 specifying the average day, and then specify this day as 3 average days in the appropriate field. In such a case, the minimum stocked number would be three times the calculated average daily dispensing frequency value for prescription items falling within the selected grid cell.

To provide an illustrative example, a user may select grid cell 415.3 and select only the "max daily" option from interactive cell options field 422, specifying the number of occurrences as 2. Although not shown in FIG. 4B for purposes of brevity, a tolerance number may also be specified by a user, for example. Alternatively, a default tolerance may be used (e.g., 10%). As discussed above with reference to FIG. 2, the maximum daily dispensing frequency value may be calculated by taking the average of the 2 top daily dispensing frequency values within 10% of one another over the sampling period. This advantageously filters out any outliers from the calculation of the maximum daily dispensing frequency value, providing a more accurate count to use as the minimum stocked number.

To provide another illustrative example, a user may select grid cell 415.4 and, in addition to selecting the "max daily" option described directly above, select the "average day" option from interactive cell options field 422 and specify the average number of days as 3. In this case, the calculated minimum stocked number would be calculated as the greater of 3 times the calculated average daily dispensing frequency value or the maximum daily dispensing frequency value for the 2 top occurrences within 10 percent of one another for prescription items falling within grid cell 415.4.

To provide yet another illustrative example, a user may select grid cell 415.5 and, in addition to selecting the "average day" option from interactive cell options field 422, may also select the "max daily aver. of top x occurrences" option and specify the number of occurrences as 10. As discussed above with reference to FIG. 2, the maximum average daily dispensing frequency value may be calculated by averaging the top 10 highest daily dispensing frequency values within the sampling period (e.g., summing these values and dividing by 10). In this case, the minimum stocked number would be calculated as the greater of 3 times the calculated average daily dispensing frequency value or the maximum average daily dispensing frequency value calculated from the top 10 occurrences within the sampling period.

A user may repeat this process to assign cell options to each grid cell within grid 415. In this way, a complete rule may be established for an entire pharmacy's stock regarding a minimum stocked number that triggers the generation and/or transmission of a purchase order for qualifying prescription items associated with the ranges of each grid cell specified in grid 415. The user interface may then be further utilized to specify, for prescription items that qualify for automatic stock tracking, ordering, and replenishment, additional rule parameters to specify the maximum stock number to keep on hand. This is further discussed below with reference to FIG. 4C.

Again, the range of costs used to qualify various prescribed items may be any suitable unit such as single dosages, packs, bottles, etc. As a result, embodiments include the calculated maximum number of a prescribed item facilitating an optimum amount of a prescribed item regardless of how that particular item is dispensed. For example, the cost used on the grid may represent the cost per dispensing unit (e.g., per tablet, per milliliter, per inhaler, etc.) as opposed to the cost of prepackaged prescription items (e.g., per pack or per bottle). Therefore, embodiments include the stock replenishment process calculating and ordering a number of equivalent prepackaged prescription items such that, when delivered, the total number of stocked prescription items per dispensing unit will reach the specified calculated maximum. For example, the minimum and maximum values may be expressed in terms of a number of dispensing units (tablets, caplets, etc.), but when re-ordered, the purchase order may include a quantity expressed in packs, each pack having multiple dispensing units.

Figure 4C:
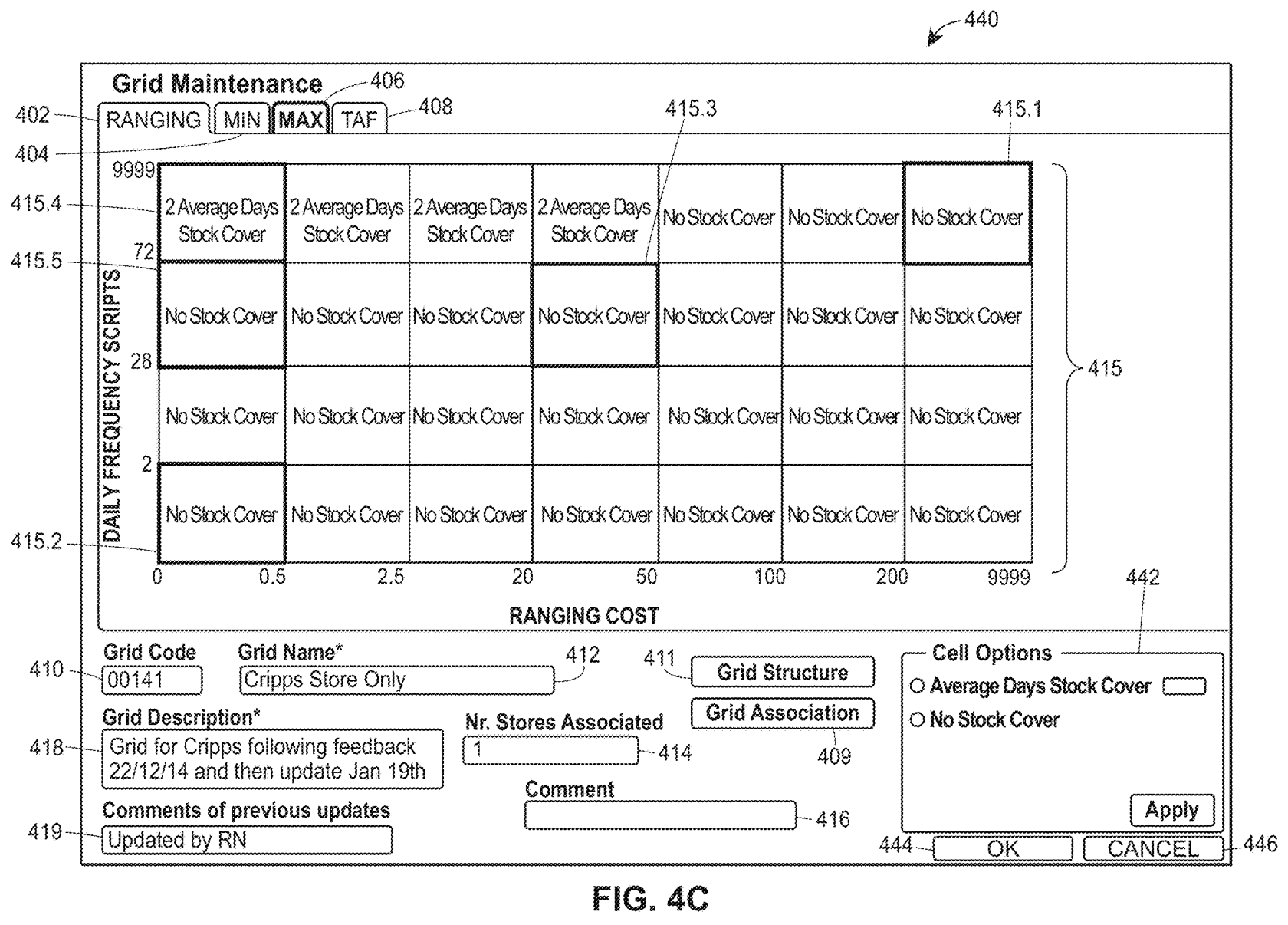

FIG. 4C illustrates an exemplary user interface screen 440 to facilitate the calculation of a maximum stocked number for a qualifying prescription item in accordance with an exemplary embodiment of the present disclosure. In an embodiment, exemplary user interface screen 440 corresponds to a transition from exemplary user interface screen 400, 440, or 460 due to a user selecting tab 406 while in the other exemplary user interface screen. As discussed above, exemplary user interface 440 shares several portions with other exemplary user interfaces. For example, grid association interactive button 409, grid code field 410, grid structure interactive button 411, grid name interactive field 412, number of stores field 414, interactive comments field 416, interactive grid description field 418, and update comments field 419 are also displayed in exemplary user interface 440. These portions may perform the same functions as discussed above with reference to FIGS. 4A and 4B.

However, exemplary user interface 440 also includes an interactive cell options field 442, which a user may utilize to set the various rule parameters for each prescription item in grid 415 that qualifies for automatic stock tracking and replenishment. For example, interactive cell options field 424 provides a user with the option to select one of the grid cells within grid 415 and to identify that grid cell as having a number of days of average stock cover or no stock cover. In an embodiment, grid cells that do not qualify for automatic stock tracking, ordering, and replenishment may be set to "no stock cover" by default. Upon selecting the average days of stock cover option, a user may specify a number of days and select the interactive "ok" button 444 to apply these selections to an individual grid cell. Alternatively, a user may select the interactive "cancel" button to 446 such that no changes are made to grid 415.

To provide an illustrative example, a user may select grid cell 415.4 and specify the number of days of stock cover as 2. The maximum stocked number may be calculated based upon a multiple (in this case a multiple of 2) of the average daily dispensing frequency value, which may be the same average daily dispensing frequency value that is used in the calculation of the minimum stocked number. The maximum stocked number may then be calculated using Eqn. 1 above, as previously discussed with reference to FIG. 2.

A user may repeat this process to assign cell options to each grid cell within grid 415. In this way, a complete rule set is established for an entire pharmacy's stock regarding a maximum stocked number of prescription item stock to maintain for qualifying prescription items associated with the ranges of each grid cell specified in FIG. 4A. The user interface may then be further utilized to specify, for prescription items that qualify for automatic stock tracking, ordering, and replenishment, additional parameters to specify exceptions to the various rules as discussed herein with respect to FIGS. 4A-4C. This is further discussed below with reference to FIG. 4D.

FIG. 4D illustrates an exemplary user interface screen 460 to facilitate the calculation of one or more rule exceptions to apply to one or more qualifying prescription items in accordance with an exemplary embodiment of the present disclosure. In an embodiment, exemplary user interface screen 460 corresponds to a transition from exemplary user interface screen 400, 420, or 440 due to a user selecting tab 408 while in the other exemplary user interface screen. As discussed above, exemplary user interface 460 shares several portions with other exemplary user interfaces. For example, grid association interactive button 409, grid code field 410, grid structure interactive button 411, grid name interactive field 412, number of stores field 414, interactive comments field 416, interactive grid description field 418, and update comments field 419 are also displayed in exemplary user interface 440. These portions may perform the same functions as discussed above with reference to FIGS. 4A-C.

However, exemplary user interface 460 also includes an interactive cell options field 462, which a user may utilize to set the various exception parameters for each prescription item in grid 415 that qualifies for automatic stock tracking and replenishment. For example, interactive cell options field 462 provides a user with the option to select a "trade adjustment factor" (TAF) uplift to one or more of the grid cells within grid 415. In an embodiment, grid cells that do not qualify for automatic stock tracking, ordering, and replenishment may be set to "no TAF uplift" by default. Upon selecting the TAF uplift option, a user may select the "apply" button to apply these selections to an individual grid cell.

To provide an illustrative example, a user may select grid cell 415.4 and apply a TAF uplift, which may be a default value or otherwise specified by a user as desired. Although not illustrated in FIG. 4D for purposes of brevity, the TAF uplift may be associated with a user-specified period of time, a default period of time, specific pharmacies or stores, specific groups of pharmacies or stores, specific countries, regions, etc. The TAF uplift may function as an override, to increase or decrease the calculated minimum and/or maximum stocked numbers of prescription items for short durations throughout the year that provide inaccurate, erratic, or unpredictable transactional data. The TAF uplift may additionally or alternatively allow the calculated minimum and/or maximum stocked numbers of prescription items to be calculated using prescribed item transaction data from a large group of stores or pharmacies, but allow for adjustments to be applied as another layer of rules to subsets of those stores. In this way, the TAF may provide additional convenience and customization when managing stock for a large number of pharmacies that may span several regions, states, countries, etc.

Although interactive cell options field 462 is shown in FIG. 4D as having only two selectable options, embodiments include interactive cell options field 462 having any suitable number of options to facilitate the entry and application of various rule exception parameters. For example, calculated minimum and maximum stocked numbers may be increased or decreased for particular grid cells, over specific dates, and/or for specific stores. To provide another example, the qualifying ranges of average daily dispensing frequency values and/or cost ranges may be adjusted over specific dates and/or for specific stores, etc.

Figure 5:
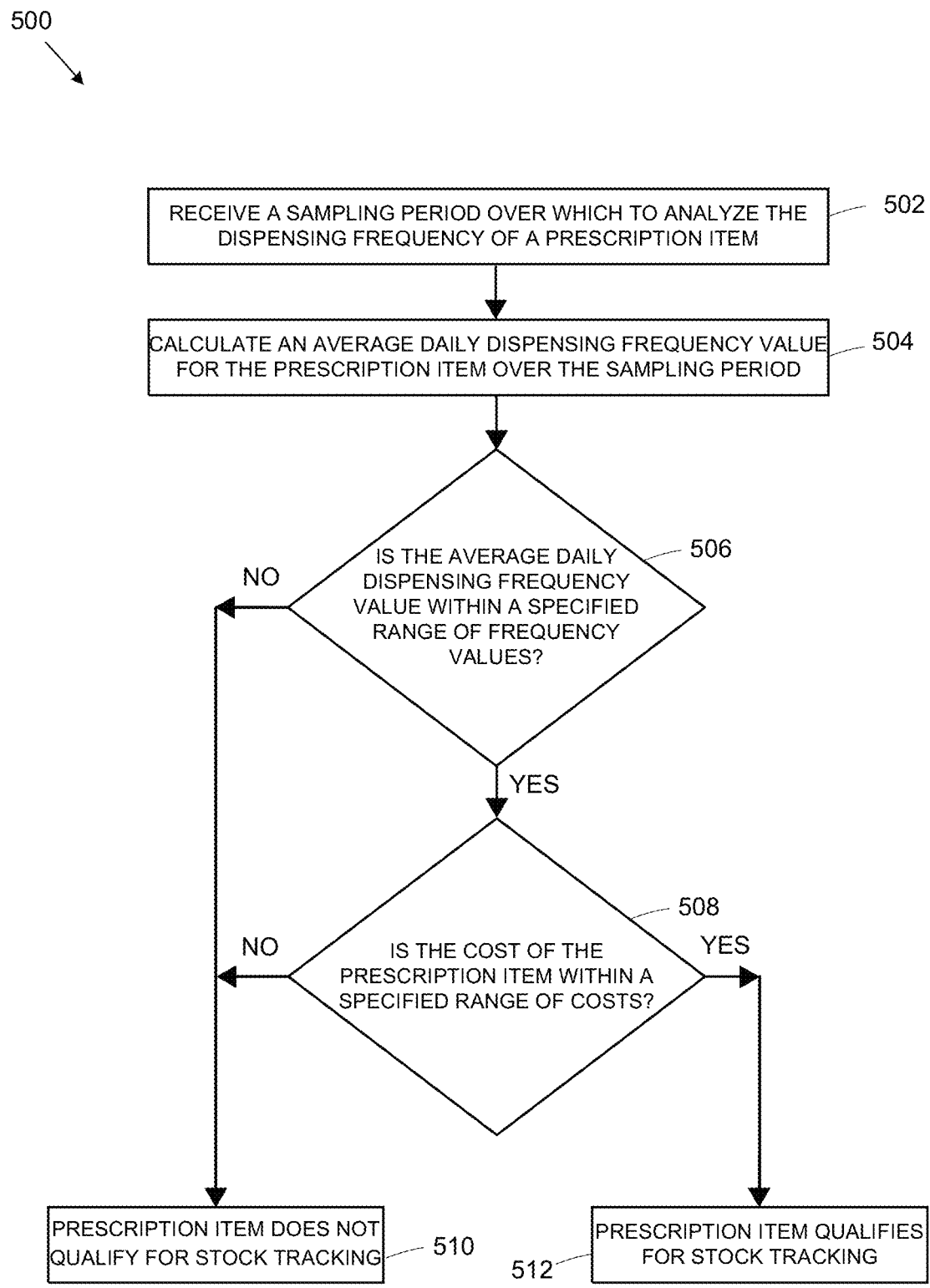
FIG. 5 illustrates an exemplary method 500 in accordance with an exemplary embodiment of the present disclosure.

FIG. 5 illustrates an exemplary method 500 in accordance with an exemplary embodiment of the present disclosure. In an embodiment, method 500 may be implemented by any suitable device, such as one or more external computing devices 114.1-114.N and/or one or more pharmacy computing devices, such as computing devices 104.1-104.M, for example, as shown in FIG. 1. In an embodiment, method 500 may be performed by any suitable combination of one or more processors, applications, algorithms, and/or routines, such as any processor 202 executing instructions stored in memory 210 in conjunction with data received via communication unit 204, for example.

Method 500 may start when one or more processors receive a sampling period over which to analyze a dispensing frequency of a prescription item (block 502). This may include, for example, a user providing the sampling period via a suitable user interface (e.g., one associated with a pharmacy computing device, such as one or more computing devices 104.1-104.M, as shown in FIG. 1) and communicating this sampling period to another external computing device (e.g., one or more external computing devices 114.1-114.N, as shown in FIG. 1) (block 502). This may also include, for example, an application installed on an external computing device providing a default sampling period (block 502). Again, the sampling period may be any suitable sampling period, such as 30 days, 6 months, 1 year, etc.

Method 500 may include one or more processors calculating an average daily dispensing frequency value for the prescription item over the sampling period (block 504). For example, for a 30 day sampling period, a specific prescription drug may be dispensed a total of 300 times. In such a case, the average daily dispensing frequency value for that prescription item would be 10 prescription items dispensed per day.

Method 500 may include one or more processors determining whether the average daily dispensing frequency value for the prescription item (block 504) is within a specified range of frequency values (i.e., ranging frequency) (block 506). This may include, for example, a determination of whether a particular prescribed item is dispensed at an average daily dispensing frequency that falls with a range of average daily dispensing frequency values specified by a user (block 506). For example, a user may provide the range of average daily dispensing frequency values in accordance with the creation of a number of grid cells, as discussed above with reference to FIG. 4A. If the average daily dispensing frequency value for the prescription item falls within the specified range of average daily dispensing frequency values, the prescription item potentially qualifies for automated stock tracking, ordering, and replenishment, and method 500 may continue to determine whether the cost of the prescription item is also within a range of costs to verify this (block 508). Otherwise, the prescription item does not qualify for automatic prescription stock tracking, ordering, and replenishment (block 510).

Method 500 may include one or more processors determining whether the cost of the prescription item is within a specified range of costs (block 508). This may include, for example, a determination of whether a prescription item that potentially qualifies for automated stock tracking, ordering, and replenishment (block 506) actually qualifies due to the cost of the potentially qualifying prescription item having a cost that falls with a range of costs specified by a user (block 508). For example, a user may provide the range of costs in accordance with the creation of a number of grid cells, which intersect with the specified range of average daily dispensing frequency values as discussed above with reference to FIG. 4A. If the cost of the prescription item falls within the specified range of costs, then method 500 may continue such that the prescription item qualifies for automated stock tracking, ordering, and replenishment (block 512). Otherwise, the prescription item does not qualify for automatic stock tracking, ordering, and replenishment (block 510).

Method 500 may include one or more processors tracking a prescription item that qualifies for automatic stock tracking, ordering, and replenishment (block 512). This may include, for example, monitoring stock files from a pharmacy associated with the prescription item to ensure that purchase orders are generated and transmitted upon the stocked number of the tracked prescription item falling below a specified minimum stocked number, which is discussed further below with reference to FIG. 6 (block 512). This tracking may occur over any suitable sampling period, such as continuously, each day, each time a stock file is updated, at the close of business of each pharmacy, etc. (block 512).

Figure 6:
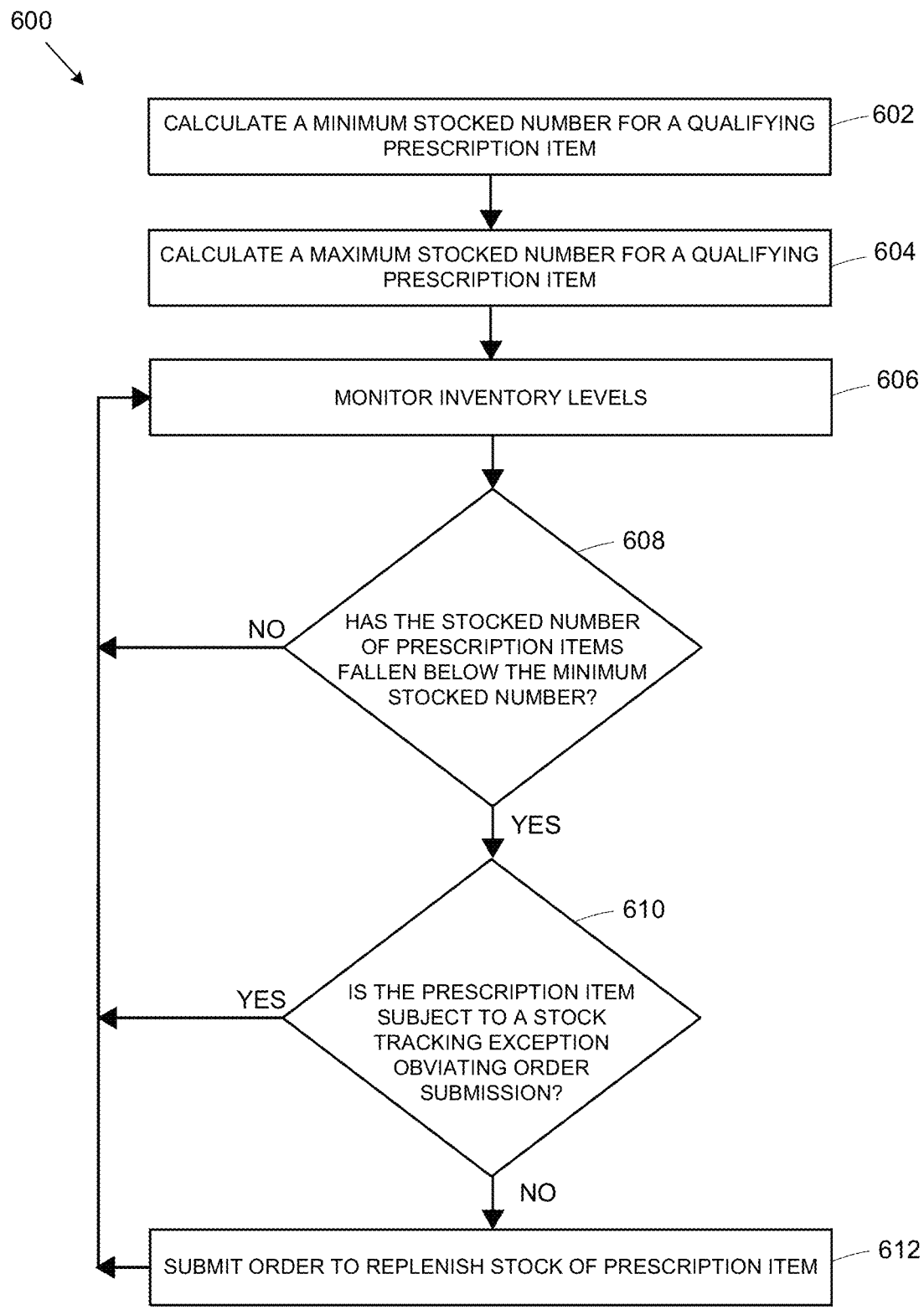
FIG. 6 illustrates an exemplary method 600 in accordance with an exemplary embodiment of the present disclosure.

FIG. 6 illustrates an exemplary method 600 in accordance with an exemplary embodiment of the present disclosure. In an embodiment, method 600 may be implemented by any suitable device, such as one or more external computing devices 114.1-114.N, for example, as shown in FIG. 1. In an embodiment, method 600 may be performed by any suitable combination of one or more processors, applications, algorithms, and/or routines, such as any processor 202 executing instructions stored in memory 210 in conjunction with data received via communication unit 204, for example. In an embodiment, method 600 may be applied to one or more prescribed items that qualify for automatic stock tracking, ordering, and replenishment, as discussed above with reference to FIG. 5 (block 512).

Method 600 may start when one or more processors calculate a minimum stocked number for a qualifying prescription item (block 602). This may include, for example, a user specifying any suitable combination of metrics derived from the prescribed item's transaction history over the sampling period, as discussed above with reference to FIG. 4B (block 604).

Method 600 may include one or more processors calculating a maximum stocked number for the qualifying prescription item (block 604). This may include, for example, a user specifying any suitable combination of metrics derived from the prescribed item's transaction history over the sampling period, as discussed above with reference to FIG. 4C (block 604).

Method 600 may include one or more processors monitoring inventory levels associated with the qualifying prescription item (block 606). Again, the monitoring may be performed over any suitable sampling period, such as continuously, each day, each time a stock file is updated, at the close of business of each pharmacy, etc. (block 606).

Method 600 may include one or more processors determining whether a stocked number of a qualifying prescription item has fallen below the minimum stocked number (block 602) to potentially require a purchase order being generated (block 608). If so, method 600 may continue to determine whether any exceptions or other factors exist for the particular prescription item (block 610). Otherwise, method 600 may revert to continuing to monitor inventory levels (block 606).

Method 600 may include one or more processors determining whether a prescription item, once its stock number has been depleted to less than the minimum stocked number (block 602) is subject to a stock tracking exception that obviates the purchase order submission (block 610). This may include, for example, one or more TAF uplifts that may apply to the particular prescription item and/or other exceptions that may be based upon dates, regions, specific stores, etc., as discussed above with reference to FIG. 4D (block 610). If one or more stock tracking exceptions do exist, method 600 may revert to continuing to monitor inventory levels (block 606). Otherwise, method 600 may continue such that a purchase order is generated and submitted to replenish the depleted stock of the prescription item (block 612).

Method 600 may include one or more processors submitting a purchase order to replenish stock of the prescription item (block 612). In some embodiments, the purchase order may be for an amount of the prescribed item such that, upon the order being fulfilled, the prescription item stock is equal to or less than the maximum (block 604) stocked number (block 612). The purchase order submission may include any suitable manual, automated, or semi-automated process that generates, transmits, or otherwise results in the stock of the prescription item being replenished, as discussed above, for example, with reference to FIG. 1 (block 612). Upon submission of a purchase order to replenish stock, method 600 may continue to monitor inventory levels (block 606), and repeat the process of monitoring, ordering, and replenishing stock as prescription items are dispensed.

As discussed above, embodiments are described to facilitate whether a prescription item qualifies for automatic stock tracking, the calculation of a minimum stocked number, the calculation of a maximum stocked number, the calculation of one or more rule exceptions to apply to one or more qualifying prescription items, etc. As discussed above, a user may specify user-defined parameters that are used in conjunction in the aforementioned calculations and determinations.

For example, a user may manually specify or select predetermined or default minimum and maximum stocked numbers of prescription items as part of the tracking and replenishment process instead of having these numbers calculated from stock item transaction data. To provide another example, a user may manually specify or select from various predetermined or default options such as a suitable sampling time period for which prescription item transaction data may be analyzed, which may differ for different prescription products and/or different pharmacy locations.

To provide additional examples, as discussed with reference to FIG. 4B, a tolerance number may also be specified by a user or a default tolerance may be used as part of the calculation of the maximum daily dispensing frequency value. To provide yet another example, as discussed with reference to FIG. 4D, the TAF uplift may be a default value or otherwise specified by a user.

Although not shown for purposes of brevity, embodiments include a suitable computing device (e.g., external computing device 114.N, as shown in FIG. 1) being configured to display an interactive product parameter screen, with which a user (e.g., user 115) may interact to specify these types of product parameters, among others. In various embodiments, the interactive product parameter screen may include any suitable user interface to allow a user to enter any suitable number and/or type of parameters that may be used as part of the rule sets to facilitate prescription item stock tracking, ordering, and replenishment. For example, upon a user specifying minimum and maximum stocked numbers of prescription items, a sampling time period for which prescription item transaction data may be analyzed, a tolerance number, a TAF uplift value, etc., the computing device may store these values as data in a suitable portion of central hosting service 114 such that the data may be accessed to implement execution of the stock management application and the various embodiments described herein.

As used herein, the term "pharmacy" may include, for example, a single outlet or a plurality of outlets affiliated with one or more entities that are licensed to dispense prescribed pharmaceutical products such as drugs, medicaments, durable medical equipment, etc. The one or more entities may be located, for example, in geographic locations separate from one another, in different areas of the same city, or in different states, countries, etc. The pharmacy outlets may include, for example, one or more of a conventional retail store, space within a location operated by another commercial or not-for-profit entity (e.g., within a discount store, hospital, school, nursing home, etc.), an outlet in proximity with a warehouse or distribution center, a call-in pharmacy, a long-term care pharmacy, a workplace/on-site pharmacy, a specialty pharmacy, etc. The pharmacy may be commercial or not-for-profit, and may provide or vend other products in addition to the prescribed pharmaceutical products.

As used herein, the term "pharmacy computing system" may include a computing system that is owned and/or operated by a pharmacy to aid pharmacy employees and representatives to fill and dispense prescribed pharmaceutical products and other products. A pharmacy computing system may include at least one computing device, database, display device, and user input interface device. Typically, each outlet of a pharmacy may have a local instance of (or local access to) a pharmacy computing system. In some embodiments, local instances of a pharmacy computing system may be networked.

Although the foregoing text sets forth a detailed description of numerous different embodiments, it should be understood that the detailed description is to be construed as exemplary only and does not describe every possible embodiment because describing every possible embodiment would be impractical, if not impossible. In light of the foregoing text, one of ordinary skill in the art will recognize that numerous alternative embodiments could be implemented, using either current technology or technology developed after the filing date of this patent application.

What is claimed is:

1. A method of performing prescription stock management, comprising:
    identifying, by one or more processors, one or more qualifying prescription items from a plurality of prescription items, each qualifying prescription item being dispensed over a sampling period at an average daily dispensing frequency value;
    calculating, by one or more processors, for a qualifying prescription item from among the qualifying prescription items, a maximum stocked number;
    calculating, by one or more processors, for the qualifying prescription item from among the qualifying prescription items, a minimum stocked number based upon forecasting future demand for the qualifying prescription item;
    transmitting, by one or more processors, an order to an external computing device when a stocked number of the qualifying prescription item is less than the minimum stocked number, and
    wherein the order, upon being fulfilled, results in a replenishment of the qualifying prescription item such that the stocked number of the qualifying prescription item is greater than the minimum stocked number and up to the maximum stocked number.

2. The method of claim 1, wherein forecasting future demand for the qualifying prescription item further comprises forecasting future demand based on applying various statistical analyses to transactions of the qualifying prescription item.

3. The method of claim 1, wherein forecasting future demand for the qualifying prescription item further comprises forecasting future demand based on recent changes in the dispensation rate of the qualifying prescription item.

4. The method of claim 1, further comprising:
    calculating, by one or more processors, a multiple of the average daily dispensing frequency value of the qualifying prescription item; and
    calculating, by one or more processors, the maximum stocked number as a sum of (i) the minimum stocked number of the qualifying prescription item, and (ii) the multiple of the average daily dispensing frequency value of the qualifying prescription item.

5. The method of claim 1 wherein forecasting future demand for the qualifying prescription item further comprises calculating, by one or more processors, a multiple of average daily dispensing frequency value of the qualifying prescription item over the sampling period.

6. The method of claim 1 wherein forecasting future demand for the qualifying prescription item further comprises:
    receiving, by one or more processors, a number of days associated with highest daily dispensing frequency values within the sampling period for the qualifying prescription item; and
    calculating, by one or more processors, a maximum average daily dispensing frequency value by averaging each of the highest daily frequency dispensing values over the number of days.

7. The method of claim 1, wherein forecasting future demand for the qualifying prescription item further comprises:
    receiving, by one or more processors, a number of daily dispensing frequency values within the sampling period for the qualifying prescription item, the number of daily dispensing frequency values corresponding to a top number of occurrences over the sampling period within a threshold variance; and
    calculating, by one or more processors, a maximum daily dispensing frequency value by averaging a sum of the daily dispensing frequency values over their number of occurrences within the sampling period.

8. A computing device that facilitates prescription stock management, comprising:
    a communication unit configured to receive a history of prescribed prescription item transactions;
    a memory configured to store the history of prescribed prescription item transactions; and
    a processor configured to:
    identify one or more qualifying prescription items from a plurality of prescription items, each qualifying prescription item being dispensed over a sampling period at an average daily dispensing frequency value,
    calculate for a qualifying prescription item from among the qualifying prescription items, a maximum stocked number, and
    calculate for the qualifying prescription item from among the qualifying prescription items, a minimum stocked number based upon forecasting future demand for the qualifying prescription item,
    wherein the communication unit is further configured to transmit an order to an external computing device when a stocked number of the qualifying prescription item is less than the minimum stocked number, and
    wherein the order, upon being fulfilled, results in a replenishment of the qualifying prescription item such that the stocked number of the qualifying prescription item is greater than the minimum stocked number and up to the maximum stocked number.

9. The computing device of claim 8, wherein the processor is further configured to forecast future demand for the qualifying prescription item based on applying various statistical analyses to transactions of the qualifying prescription item.

10. The computing device of claim 8, wherein the processor is further configured to forecast future demand for the qualifying prescription item based on recent changes in the dispensation rate of the qualifying prescription item.

11. The computing device of claim 8, wherein the processor is further configured to:
    calculate a multiple of the average daily dispensing frequency value of the qualifying prescription item; and
    calculate the maximum stocked number as a sum of (i) the minimum stocked number of the qualifying prescription item, and (ii) the multiple of the average daily dispensing frequency value of the qualifying prescription item.

12. The computing device of claim 8, wherein the processor is further configured to calculate a multiple of average daily dispensing frequency value of the qualifying prescription item over the sampling period.

13. The computing device of claim 8, wherein the processor is further configured to:
receive a number of days associated with highest daily dispensing frequency values within the sampling period for the qualifying prescription item; and
calculate a maximum average daily dispensing frequency value by averaging each of the highest daily frequency dispensing values over the number of days.

14. The computing device of claim 8, wherein the processor is further configured to:
receive a number of daily dispensing frequency values within the sampling period for the qualifying prescription item, the number of daily dispensing frequency values corresponding to a top number of occurrences over the sampling period within a threshold variance; and
calculate a maximum daily dispensing frequency value by averaging a sum of the daily dispensing frequency values over their number of occurrences within the sampling period.

15. A non-transitory, tangible computer-readable medium storing machine readable instructions that, when executed by a processor, cause the processor to:
identify one or more qualifying prescription items from a plurality of prescription items, each qualifying prescription item being dispensed over a sampling period at an average daily dispensing frequency value;
calculate for a qualifying prescription item from among the qualifying prescription items, a maximum stocked number;
calculate for the qualifying prescription item from among the qualifying prescription items, a minimum stocked number based upon forecasting future demand for the qualifying prescription item; and
transmit an order to an external computing device when a stocked number of the qualifying prescription item is less than the minimum stocked number,
wherein the order, upon being fulfilled, results in a replenishment of the qualifying prescription item such that the stocked number of the qualifying prescription item is greater than the minimum stocked number and up to the maximum stocked number.

16. The non-transitory, tangible computer-readable medium of claim 15, further including instructions that, when executed by the processor, cause the processor to forecast future demand for the qualifying prescription item based on applying various statistical analyses to transactions of the qualifying prescription item.

17. The non-transitory, tangible computer-readable medium of claim 15, further including instructions that, when executed by the processor, cause the processor to forecast future demand for the qualifying prescription item based on recent changes in the dispensation rate of the qualifying prescription item.

18. The non-transitory, tangible computer-readable medium of claim 15, further including instructions that, when executed by the processor, cause the processor to:
calculate a multiple of the average daily dispensing frequency value of the qualifying prescription item; and
calculate the maximum stocked number as a sum of (i) the minimum stocked number of the qualifying prescription item, and (ii) the multiple of the average daily dispensing frequency value of the qualifying prescription item.

19. The non-transitory, tangible computer-readable medium of claim 15, further including instructions that, when executed by the processor, cause the processor to calculate a multiple of average daily dispensing frequency value of the qualifying prescription item over the sampling period.

20. The non-transitory, tangible computer-readable medium of claim 15, further including instructions that, when executed by the processor, cause the processor to:
receive a number of days associated with highest daily dispensing frequency values within the sampling period for the qualifying prescription item; and
calculate a maximum average daily dispensing frequency value by averaging each of the highest daily frequency dispensing values over the number of days.

* * * * *